US011211805B2

(12) United States Patent
Fishler

(10) Patent No.: US 11,211,805 B2
(45) Date of Patent: Dec. 28, 2021

(54) METHODS, SYSTEMS, AND DEVICES THAT ESTIMATE LONGEVITY OF AN IMPLANTABLE MEDICAL DEVICE

(71) Applicant: Pacesetter, Inc., Sylmar, CA (US)

(72) Inventor: Matthew G. Fishler, Scotts Valley, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 16/894,281

(22) Filed: Jun. 5, 2020

(65) Prior Publication Data
US 2020/0403429 A1    Dec. 24, 2020

Related U.S. Application Data

(60) Provisional application No. 62/864,359, filed on Jun. 20, 2019.

(51) Int. Cl.
*G01R 31/36* (2020.01)
*H02J 7/00* (2006.01)
(Continued)

(52) U.S. Cl.
CPC ............ *H02J 7/0048* (2020.01); *A61N 1/378* (2013.01); *A61N 1/3708* (2013.01); *A61N 1/37252* (2013.01); *G01R 31/36* (2013.01); *G05B 15/02* (2013.01); *G06Q 10/20* (2013.01); *G16H 40/40* (2018.01); *H04Q 9/02* (2013.01); *A61N 1/3925* (2013.01); *A61N 1/3956* (2013.01); *G01R 31/382* (2019.01); *G01R 31/392* (2019.01);
(Continued)

(58) Field of Classification Search
CPC ........ A61N 1/37; A61N 1/3708; G01R 31/36; G01R 31/382; G01R 31/3828; G01R 31/392; H02J 7/0048
See application file for complete search history.

(56) References Cited

U.S. PATENT DOCUMENTS

| | | | |
|---|---|---|---|
| 4,952,862 A * | 8/1990 | Biagetti | G01R 31/3648 |
| | | | 320/132 |
| 6,400,988 B1 | 6/2002 | Gurewitsch | |
| (Continued) | | | |

FOREIGN PATENT DOCUMENTS

| | | |
|---|---|---|
| EP | 2250513 B1 | 12/2014 |
| EP | 2219730 B1 | 1/2015 |

*Primary Examiner* — Benyam Haile
(74) *Attorney, Agent, or Firm* — Vierra Magen Marcus LLP

(57) ABSTRACT

Described herein are methods, devices, and systems that estimate a total amount of time it takes to discharge a battery of an IMD from initial to subsequent capacity levels, which total amount of time is indicative of a longevity of the IMD. In certain embodiments, a range of capacity levels for the battery is separated into N separate intervals. For each of the N intervals, an estimate of an amount of time it takes for the battery to discharge from a beginning to an end of the interval is determined, to thereby determine N amounts of time that are summed to estimate the total amount of time that it takes to discharge the battery from the initial to subsequent capacity levels. In other embodiments, an iterative equation is used to estimate the total amount of time takes it takes to discharge the battery from the initial to subsequent capacity levels.

23 Claims, 6 Drawing Sheets

(51) Int. Cl.
*G06Q 10/00* (2012.01)
*G16H 40/40* (2018.01)
*G05B 15/02* (2006.01)
*H04Q 9/02* (2006.01)
*A61N 1/372* (2006.01)
*A61N 1/37* (2006.01)
*A61N 1/378* (2006.01)
*A61N 1/39* (2006.01)
*G01R 31/392* (2019.01)
*G01R 31/382* (2019.01)

(52) U.S. Cl.
CPC ............ *H04Q 2213/002* (2013.01); *H04Q 2213/13175* (2013.01)

(56) References Cited

U.S. PATENT DOCUMENTS

| | | | |
|---|---|---|---|
| 6,671,552 | B2 | 12/2003 | Merritt et al. |
| 6,760,625 | B1 | 7/2004 | Kroll |
| 6,804,557 | B1 | 10/2004 | Kroll |
| 8,131,365 | B2 | 3/2012 | Zhang et al. |
| 8,214,164 | B2 | 7/2012 | Gandhi et al. |
| 8,494,633 | B2 | 7/2013 | Tobacman |
| 8,868,187 | B2 | 10/2014 | Gandhi et al. |
| 9,616,238 | B2 | 4/2017 | Demmer et al. |
| 10,022,548 | B2 | 7/2018 | Brooke et al. |
| 10,197,629 | B2 | 2/2019 | Gordon et al. |
| 2011/0130984 | A1* | 6/2011 | Schmidt ............ A61N 1/37252 702/63 |
| 2018/0372805 | A1 | 12/2018 | Fischer et al. |

\* cited by examiner

_US 11,211,805 B2_

METHODS, SYSTEMS, AND DEVICES THAT ESTIMATE LONGEVITY OF AN IMPLANTABLE MEDICAL DEVICE

PRIORITY CLAIM

This application claims priority to U.S. Provisional Patent Application No. 62/864,359, filed Jun. 20, 2019, which is incorporated herein by reference in its entirety.

FIELD OF TECHNOLOGY

Embodiments of the present technology described herein generally relate to methods, systems and devices that can be used to estimate a longevity of an implantable medical device (IMD).

BACKGROUND

Implantable medical devices (IMDs) are typically battery powered devices that are implanted within a patient's body to have therapy available to the patient on a continuous basis. Battery failure is a particular problem with these devices as replacement of batteries often requires invasive surgical procedures. One particularly common type of IMD is an implantable cardiac stimulation device.

Implantable cardiac stimulation devices, such as pacemakers and implantable cardioverter/defibrillators (ICD's), are employed to monitor cardiac activity and to provide therapy for patients with a variety of heart arrhythmias. Typically, these IMDs include sensors, that sense heart function and physiological parameters, and waveform generation and delivery systems, that provide electrical waveforms to the heart to correct arrhythmias and to ensure that more proper function of the heart is maintained. Because IMDs are implanted in a patient, it is desirable that the IMDs be as small and lightweight as possible in order to minimize impact on the patient. This is especially the case with leadless pacemakers.

Implantable cardiac stimulation devices are typically provided with batteries to power the monitoring and therapy delivery circuits. Due to the size constraints, the batteries used in implantable cardiac stimulation devices must be very small in size and yet able to provide power over a long period of time. Once the device is implanted, replacement of batteries typically involves invasive surgery. Hence, there is a strong desire to have small batteries that can provide significant power output to power the implantable device for extended periods of time. Known pacemaker devices typically use lithium batteries, such as lithium iodine (Lip, or lithium carbon monofluoride (Li-CFx) batteries. Lithium batteries offer relatively high energy storage density and have known, predictable discharge characteristics.

It is often important to be able to predict the longevity (e.g., remaining longevity) of a battery powered IMD, and for an external programmer (or another device and/or user interface) to present this projected longevity estimate to a user (e.g., a clinician and/or physician) so that they can make informed clinical decisions. While various methods, systems, and devices exist for predicting the remaining longevity of battery powered IMDs, they typically rely on oversimplifications that introduce errors into longevity predictions. Accordingly, it would be desirable to provide methods, systems, and devices that provide more accurate predictions of IMD longevity. Predicting remaining device longevity is also referred to herein as estimating remaining longevity.

SUMMARY

Described herein are methods, devices, and systems that estimate longevity (e.g., remaining longevity) of an implantable medical device (IMD) that is powered by a battery, which can also be referred to as a battery powered IMD. In accordance with certain embodiments, such a method involves separating a range of capacity levels for the battery of the IMD, which said range extends from an initial capacity level ($Q_i$) for the battery to a subsequent capacity level ($Q_f$) for the battery, into a number (N) of separate intervals ($int_1$, $int_2$, ... $int_N$), wherein N is an integer that is equal to or greater than 3, and wherein for each interval of the N intervals, there is a respective beginning and end of the interval and a respective estimated current ($I_{IMD}$) consumed by the IMD during the interval that may differ from a current consumed by the IMD during other ones of the N intervals. The method also includes determining, for each interval of the N intervals, an amount of time ($\Delta t$) that it takes for the battery to discharge from the beginning of the interval to the end of the interval, and thereby determining N amounts of time ($\Delta t_{int1}$, $\Delta t_{int2}$, ... $\Delta t_{intN}$). The method further includes summing the determined N amounts of time ($\Delta t_{int1}$, $\Delta t_{int2}$, ... $\Delta t_{intN}$) to thereby determine an estimate of a total amount of time ($T_{Qi \to Qf}$) that it takes to discharge the battery from the initial capacity level ($Q_i$) to the subsequent capacity level ($Q_f$), wherein the total amount of time ($T_{Qi \to Qf}$) is indicative of a longevity of the IMD that is powered by the battery.

The initial capacity level ($Q_i$) for the battery of the IMD can correspond, e.g., to a capacity level of the battery at a Beginning of Service (BOS), a capacity level of the battery at a present time, or some other specified capacity level. The subsequent capacity level ($Q_f$) for the battery of the IMD can correspond, e.g., to a capacity level of the battery at a Recommended Replacement Time (RRT), a capacity level at an End of Service (EOS), or some other specified capacity level that differs from the initial capacity level ($Q_i$). In certain embodiments, capacity levels are specified in terms of consumed capacity, such that the initial capacity level $Q_i$ (before any capacity has been consumed or otherwise discharged) can be zero (i.e., zero capacity consumed in mAhr, or zero percent depth of discharge) and the subsequent capacity level ($Q_f$) is a value greater than zero (e.g., 250 mAhr, or 99 percent depth of discharge). This is the case in the graphs shown FIGS. 1A, 1B, 2A, and 2B. In alternative embodiments, capacity levels can be specified in terms of remaining capacity, such that the initial capacity level $Q_i$ (before any capacity has been consumed or otherwise discharged) can be maximum for a new battery (e.g., 250 mAhr remaining, or 100 percent capacity remaining), and the subsequent capacity level ($Q_f$) is less than the initial capacity level. For the remaining discussion, unless stated otherwise, it is assumed that capacity levels are specified in terms of consumed capacity.

In accordance with certain embodiments, the determining, for each interval of the N intervals, the amount of time ($\Delta t$) that it takes for the battery to discharge from the beginning of the interval to the end of the interval, comprises determining a quotient of a total capacity consumed during the interval divided by the respective estimated current ($I_{IMD}$) consumed by the IMD during the interval.

In accordance with certain embodiments, the separating the range of capacity levels for the battery into the N separate intervals is performed such that for each interval, of the N intervals, the current ($I_{IMD}$) consumed by the IMD remains substantially constant during the interval. Depending upon the specific implementation, sizes of the N of separate intervals ($int_1, int_2, \ldots int_N$) can be the same as or different from one another.

In accordance with certain embodiments, at any point in time current consumed by the IMD is substantially the same as current drawn from the battery, and a performance profile for the battery is dependent on the current drawn from the battery, and thus, is dependent on the current consumed by the IMD. In certain such embodiments, for each interval of the N intervals, when determining the amount of time ($\Delta t$) that it takes for the battery to discharge from the beginning of the interval to the end of the interval, a respective portion of the performance profile for the battery that corresponds to the current being drawn from the battery during the interval is used.

In accordance with certain embodiments, the steps of determining, for each interval of the N intervals, the amount of time ($\Delta t$) that it is estimated to take for the battery to discharge from the beginning of the interval to the end of the interval, and the summing the determined N amounts of time ($\Delta t_{int1}, \Delta t_{int2}, \ldots \Delta t_{intN}$) to thereby determine the estimate of the total amount of time ($T_{Qi \to Qf}$) that it takes to discharge the battery from the initial capacity level ($Q_i$) to the subsequent capacity level ($Q_f$), are collectively performed using the following equation:

$$T_{Qi \to Qf} = \frac{\Delta Q_{int1}}{I_{IMD\_int1}} + \frac{\Delta Q_{int2}}{I_{IMD\_int2}} + \ldots + \frac{\Delta Q_{intN}}{I_{IMD\_intN}},$$

where $I_{IMD\_int\_n}$ is an estimate of the current consumed by the IMD during one of the N intervals ($int_1, int_2, \ldots int_N$), and $\Delta Q_{intn}$, is an estimate of a change in capacity (e.g., the capacity consumed) during the $n^{th}$ one of the N intervals ($int_1, int_2, \ldots int_N$). Alternatively, such steps are collectively performed using the following equation:

$$T_{Qi \to Qf} \approx \sum_{Q=Q_i}^{Q_f} \frac{\Delta Q}{I_{IMD}(V_{batt}(Q))},$$

where $I_{IMD}(V_{batt}(Q))$ is a current consumed by the IMD determined at least in part as a function of voltage of the battery at the capacity level Q. In certain embodiments, the estimate of the change in capacity during the $n^{th}$ one of the N intervals, i.e., $\Delta Q_{intn}$, is an estimate of the capacity consumed during the $n^{th}$ interval.

In accordance with certain embodiments, the above summarized methods are performed by an external device configured to wireless communicate with the IMD that is powered by the battery, and such a method further comprises outputting, via a user interface of the external device, an indication of the total amount of time ($T_{Qi \to Qf}$) that it is estimated to take to discharge the battery from the initial capacity level ($Q_i$) to the subsequent capacity level ($Q_f$).

In accordance with certain embodiments, an external device of an embodiment of the present technology includes a telemetry subsystem, a display, and at least one processor. Such an external device can be, e.g., an external clinical programmer, an in-home monitor, or a mobile computing device, but is not limited thereto. The telemetry subsystem is configured to wirelessly communication with an IMD that is powered by a battery and implanted within a patient. The at least one processor is communicatively coupled to the telemetry subsystem and the display. Further, the at least one processor is configured to separate a range of capacity levels for the battery of the IMD, which said range extends from an initial capacity level ($Q_i$) for the battery to a subsequent capacity level ($Q_f$) for the battery, into a number (N) of separate intervals ($int_1, int_2, \ldots int_N$), wherein N is an integer that is equal to or greater than 3, and wherein for each interval of the N intervals, there is a respective beginning and end of the interval and a respective estimated current ($I_{IMD}$) consumed by the IMD during the interval that may differ from a current consumed by the IMD during other ones of the N intervals. Further, the at least one processor is configured to determine, for each interval of the N intervals, an amount of time ($\Delta t$) that it is estimated to take for the battery to discharge from the beginning of the interval to the end of the interval, and thereby determines N amounts of time ($\Delta t_{int1}, \Delta t_{int2}, \ldots \Delta t_{intN}$) Additionally, the at least one processor is configured to sum the determined N amounts of time ($\Delta t_{int1}, \Delta t_{int2}, \ldots \Delta t_{intN}$) to thereby determine an estimate of a total amount of time ($T_{Qi \to Qf}$) that it takes to discharge the battery from the initial capacity level ($Q_i$) to the subsequent capacity level ($Q_f$), wherein the total amount of time ($T_{Qi \to Qf}$) is indicative of a longevity of the IMD that is powered by the battery. Further, the at least one processor is configured to cause to be displayed, on the display, an indication of the total amount of time ($T_{Qi \to Qf}$) that it is estimated to take to discharge the battery from the initial capacity level ($Q_i$) to the subsequent capacity level ($Q_f$), which is indicative of the longevity of the IMD that is powered by the battery.

In accordance with certain embodiments, the at least one processor is configured to determine, for each interval of the N intervals, the amount of time ($\Delta t$) that it is estimated to take for the battery to discharge from the beginning of the interval to the end of the interval, and is configured to sum the determined N amounts of time ($\Delta t_{int1}, \Delta t_{int2}, \ldots \Delta t_{intN}$) to thereby determine the estimate of the total amount of time ($T_{Qi \to Qf}$) that it takes to discharge the battery from the initial capacity level ($Q_i$) to the subsequent capacity level ($Q_f$), using the following equation:

$$T_{Qi \to Qf} = \frac{\Delta Q_{int1}}{I_{IMD\_int1}} + \frac{\Delta Q_{int2}}{I_{IMD\_int2}} + \ldots + \frac{\Delta Q_{intN}}{I_{IMD\_intN}},$$

where $I_{IMD\_int\_n}$ is a current consumed by the IMD during one of the N intervals ($int_1, int_2, \ldots int_N$). Alternatively, the at least one processor can be configured to use the following equation:

$$T_{Qi \to Qf} \approx \sum_{Q=Q_i}^{Q_f} \frac{\Delta Q}{I_{IMD}(V_{batt}(Q))},$$

where $I_{IMD}(V_{batt}(Q))$ is a current consumed by the IMD as a function of voltage of the battery at the capacity level Q.

Alternative methods of the present technology compute the following iterative equation: $Q_{n+1} = Q_n + I_{IMD}(V_{batt}(Q_n)) \cdot \Delta t$, with $Q_n$ initialized with a specified initial capacity level ($Q_i$) for the battery, and the iterative equation being repeatedly computed until $Q_{n+1}$ reaches a specified subsequent capacity level ($Q_f$) for the battery, where $Q_n$ is a specified capacity level for the battery that changes from one iteration of the iterative equation to a next iteration of the iterative equation, $\Delta t$ is a specified duration of time that remains the same from one iteration of the iterative equation to a next iteration of the iterative equation, $V_{batt}(Q_n)$ is a voltage of the battery at the capacity level $Q_n$, $(V_{batt}(Q_n))$ is a current consumed by the IMD as a function of the voltage of the battery at the capacity level $Q_n$, and N is how many iterations of the iterative equation are computed until $Q_{n+1}$ reaches the specified subsequent capacity level $(Q_f)$ for the battery. Such a method also includes determining a product of N multiplied by the specified duration of time ($\Delta t$) to thereby determine an estimate of a total amount of time $(T_{Qi \to Qf})$ that it takes to discharge the battery from the initial capacity level $(Q_i)$ to the subsequent capacity level $(Q_f)$, wherein the total amount of time $(T_{Qi \to Qf})$ is indicative of a longevity of the IMD that is powered by the battery.

As was also the case in the above summarized methods, the initial capacity level $(Q_i)$ for the battery of the IMD can correspond, e.g., to a capacity level of the battery at a Beginning of Service (BOS), a capacity level of the battery at a present time, or some other specified capacity level. The subsequent capacity level $(Q_f)$ for the battery of the IMD can correspond, e.g., to a capacity level of the battery at a Recommended Replacement Time (RRT), a capacity level at an End of Service (EOS), or some other specified capacity level that differs from the initial capacity level $(Q_i)$.

In accordance with certain embodiments, when $Q_{n+1}$ does not fall exactly on $Q_f$ during a last iteration of the iterative equation, interpolation is used to determine a fractional value of $\Delta t$ corresponding to a last iteration of computing the iterative equation. In such an embodiments, the fractional value of $\Delta t$ is added to the product of $N-1$ multiplied by the specified duration of time ($\Delta t$) to thereby determine the estimate of the total amount of time $(T_{Qi \to Qf})$ that it takes to discharge the battery from the initial capacity level $(Q_i)$ to the subsequent capacity level $(Q_f)$, wherein the total amount of time $(T_{Qi \to Qf})$ is indicative of a longevity of the IMD that is powered by the battery.

In accordance with certain embodiments, such a method is performed by an external device configured to wireless communicate with the IMD that is powered by the battery, and the method further comprises outputting, via a user interface of the external device, an indication of the total amount of time $(T_{Qi \to Qf})$ that it is estimated to take to discharge the battery from the initial capacity level $(Q_i)$ to the subsequent capacity level $(Q_f)$.

In accordance with certain embodiments, an external device of an embodiment of the present technology includes a telemetry subsystem, a display, and at least one processor. Such an external device can be, e.g., an external clinical programmer, an in-home monitor, or a mobile computing device, but is not limited thereto. The telemetry subsystem is configured to wirelessly communication with an IMD that is powered by a battery and implanted within a patient. The at least one processor is communicatively coupled to the telemetry subsystem and the display. Further, the at least one processor is configured to compute the following iterative equation $Q_{n+1} = Q_n + I_{IMD}(V_{batt}(Q_n)) \cdot \Delta t$, with $Q_n$ initialized with a specified initial capacity level $(Q_i)$ for the battery, and the iterative equation being repeatedly computed until $Q_{n+1}$ reaches a specified subsequent capacity level $(Q_f)$ for the battery, where $Q_n$ is a specified capacity level for the battery that changes from one iteration of the iterative equation to a next iteration of the iterative equation, $\Delta t$ is a specified duration of time that remains the same from one iteration of the iterative equation to a next iteration of the iterative equation, $V_{batt}(Q_n)$ is a voltage of the battery at the capacity level $Q_n$, $I_{IMD}(V_{batt}(Q_n))$ is a current consumed by the IMD as a function of the voltage of the battery at the capacity level $Q_n$, and N is how many iterations of the iterative equation are computed until $Q_{n+1}$ reaches the specified subsequent capacity level $(Q_f)$ for the battery. The at least one processor is also configured to determine a product of N multiplied by the specified duration of time ($\Delta t$) to thereby determine an estimate of a total amount of time $(T_{Qi \to Qf})$ that it takes to discharge the battery from the initial capacity level $(Q_i)$ to the subsequent capacity level $(Q_f)$, wherein the total amount of time $(T_{Qi \to Qf})$ is indicative of a longevity of the IMD that is powered by the battery. Additionally, the at least one processor is configured to cause to be displayed, on the display, an indication of the total amount of time $(T_{Qi \to Qf})$ that it is estimated to take to discharge the battery from the initial capacity level $(Q_i)$ to the subsequent capacity level $(Q_f)$, which is indicative of a longevity of the IMD that is powered by the battery.

In accordance with certain embodiments, when $Q_{n+1}$ does not fall exactly on $Q_f$ during a last iteration of the iterative equation, the at least one processor is configured to use interpolation to determine a fractional value of $\Delta t$ corresponding to a last iteration of computing the iterative equation. The at least one processor is also configured to add the fractional value of $\Delta t$ to the product of $N-1$ multiplied by the specified duration of time ($\Delta t$) to thereby determine the estimate of the total amount of time $(T_{Qi \to Qf})$ that it takes to discharge the battery from the initial capacity level $(Q_i)$ to the subsequent capacity level $(Q_f)$, wherein the total amount of time $(T_{Qi \to Qf})$ is indicative of a longevity of the IMD that is powered by the battery.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

As noted above, it is often important to be able to predict or estimate the longevity (e.g., remaining longevity) of a battery powered IMD, and for an external programmer (or another device and/or user interface) to present this projected longevity estimate to a user (e.g., a clinician and/or physician) so that they can make informed clinical decisions. While various methods, systems, and devices exist for predicting the longevity of battery powered IMDs, they typically rely on oversimplifications that introduce errors into longevity predictions. Accordingly, it would be desirable to provide methods, systems, and devices that provide more accurate predictions of IMD longevity. Battery powered IMDs are also referred to herein more succinctly as IMDs, or simply as devices, which should be understandable from the context in which these terms are used.

Figure 1A:
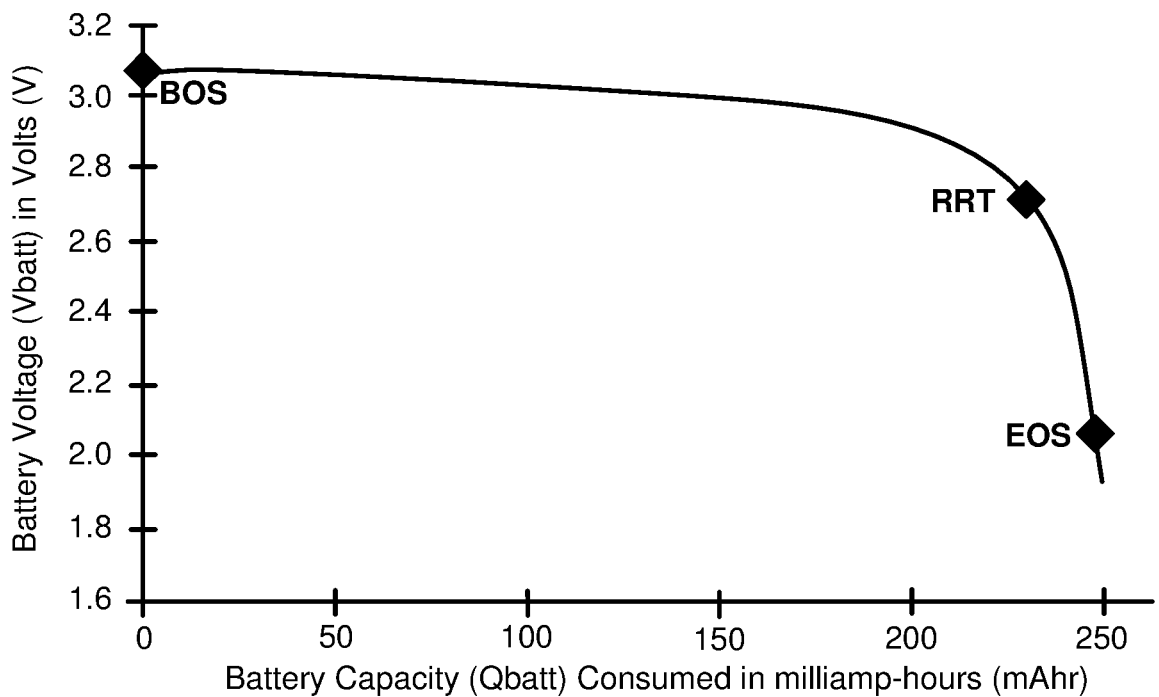
FIG. 1A illustrates an exemplary performance profile curve for an exemplary battery that is designed for an IMD, where the performance profile plots battery voltage (BV) versus battery capacity consumed.
Figure 1B:
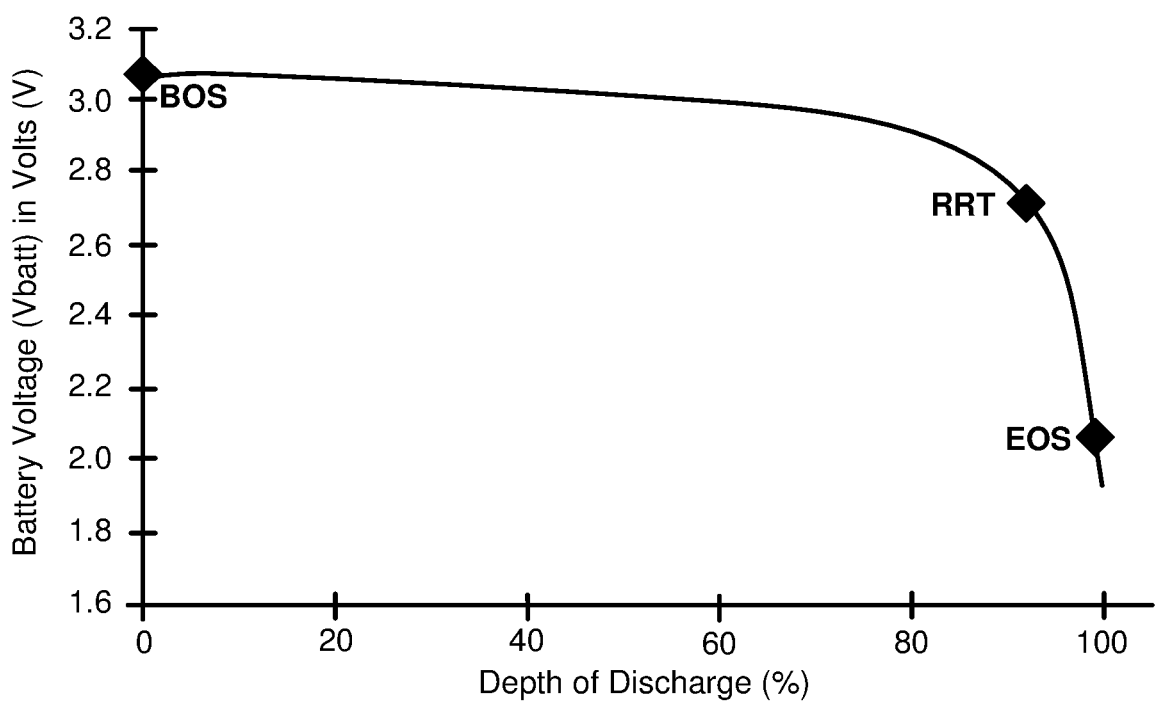
FIG. 1B illustrates an equivalent performance profile curve for the same exemplary battery as in FIG. 1A, where the performance profile plots BV versus depth of discharge.

Batteries are electrochemical systems that establish a voltage between two poles that can supply current through an external load. One means of characterizing the capabilities of a battery is via a performance profile, which plots battery voltage (BV) versus relative depth of discharge (or absolute battery capacity consumed or another equivalent metric) for a given external load, rate of discharge, etc. FIG. 1A illustrates an exemplary performance profile curve for an exemplary battery that is designed for an IMD, where the performance profile plots BV versus battery capacity consumed. FIG. 1B illustrates an equivalent performance profile curve for the same exemplary battery, where the performance profile plots BV versus depth of discharge. A few key fiducial battery stages are labeled in FIGS. 1A and 1B, including the Beginning of Service (BOS), Recommended Replacement Time (RRT), and End of Service (EOS). The BOS, which also referred to as the Beginning of Life (BOL), is the nomenclature for a new battery that has not been significantly used. The RRT, which is also known as the Elective Replacement Indicator (ERI) or Elective Replacement Time (ERT), is the nomenclature for the time at which it is recommended that an IMD containing a battery be replaced within a specified period of time (e.g., six months). The EOS, which is also known as the End of Life (EOL) or End of Service Life (EOSL), is the nomenclature for an old battery that has been depleted to the point that it could no longer reliability support basic functions. The RRT for a battery (or more generally a battery powered IMD) can occur, e.g., approximately six months prior to the EOS for the battery (or more generally, the battery powered IMD).

Referring to FIGS. 1A and 1B, the positions of the fiducials BOS, RRT, and EOS may not be inherent features of the battery, but rather may be selected by the designers based on performance requirements, and/or the like, of the IMD that the battery is powering. Thus, for example, with an EOS voltage selected at 2.1V, the total usable charge capacity (from BOS to EOS) of the battery represented in FIG. 1A is approximately 248 mAhr.

Figure 2A:
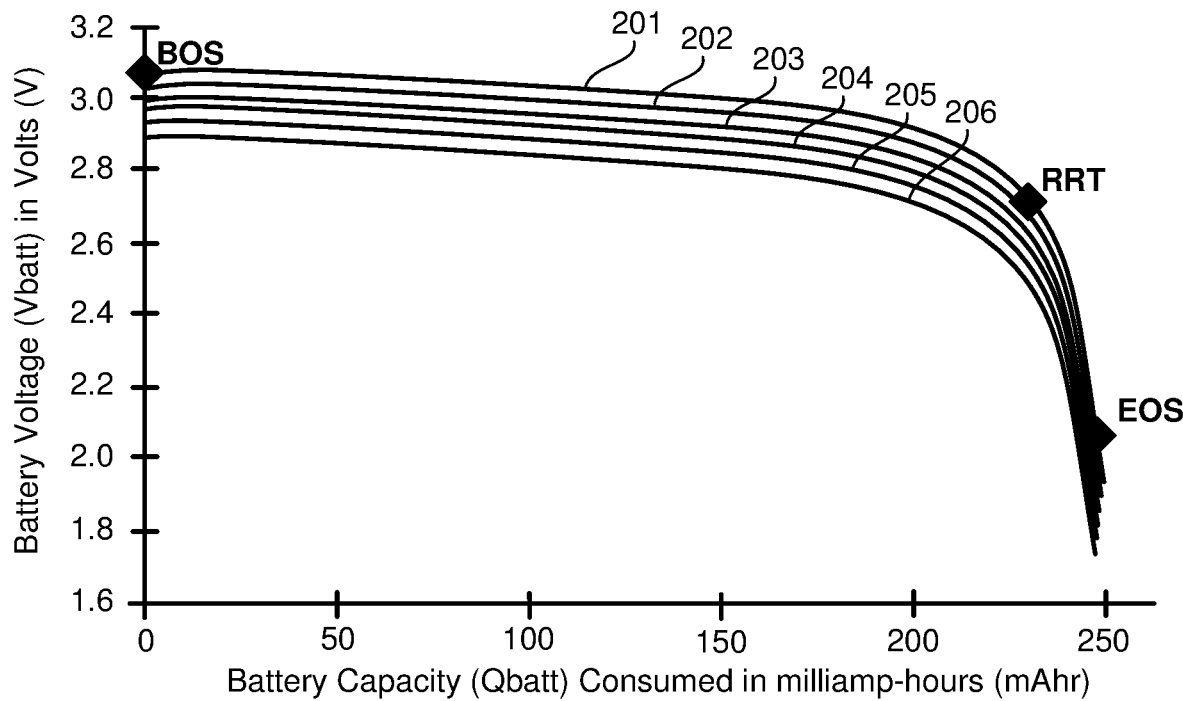
FIGS. 2A and 2B, which are similar to FIGS. 1A and 1B respectively, illustrate that battery performance profiles are themselves a function of a magnitude of a current being drawn from a battery.
Figure 2B:
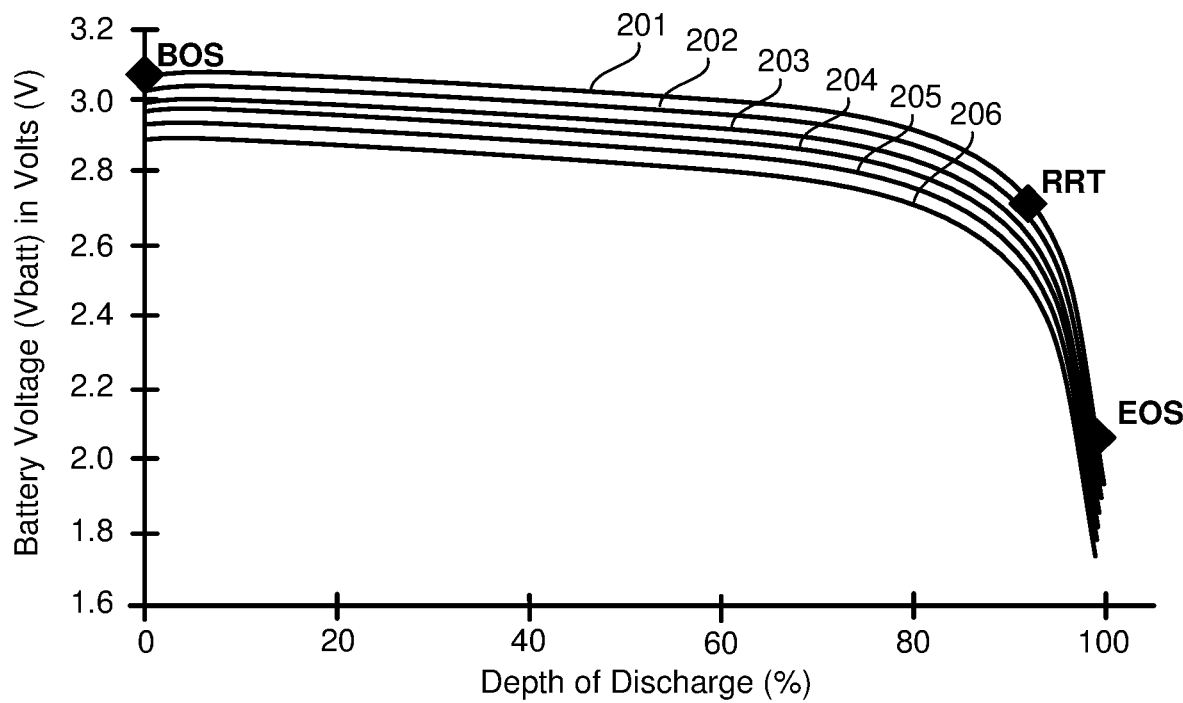

FIGS. 2A and 2B, which are similar to FIGS. 1A and 1B respectively, illustrate that battery performance profiles are themselves a function of a magnitude of a current being drawn from a battery. For example, in FIGS. 2A and 2B, the performance profile curve 201 may correspond to a current of 1 microamp (uA) being drawn from the battery, the performance profile curve 202 may correspond to a current of 2 uA being drawn from the battery, the performance profile curve 203 may correspond to a current of 5 uA being drawn from the battery, the performance profile curve 204 may correspond to a current of 10 uA being drawn from the battery, the performance profile curve 205 may correspond to a current of 20 uA being drawn from the battery, and the performance profile curve 206 may correspond to a current of 50 uA being drawn from the battery.

In FIGS. 2A and 2B, the performance profile for a battery is represented as a family of curves. Alternatively, the dependency of a battery's performance profile on the current being drawn from the battery can be represented by a three-dimensional (3D) surface, e.g., the graphs shown in FIGS. 2A and 2B can also have a z-axis corresponding to the current being drawn from the battery. Such battery profile information can be represented by an equation or stored in one or more look-up-tables (LUTs) in an IMD and/or an external device (e.g., external programmer) that is in communication with an IMD. Other variations are also possible and within the scope of the embodiments described herein. For example, another variation might be the use of one or more equations that is/are representative of the aforementioned 3D surface performance profile for a battery.

An IMD longevity estimate can be based on active programmed settings and a future projected usage profile. In its simplest form, that calculation is shown below in Equation 1:

$$\text{Remaining Longevity to } RRT = \frac{RBC_{RRT}}{I_{IMD}}. \quad \text{(Eq. 1)}$$

In Equation 1, and other equations, $RBC_{RRT}$ is the remaining battery capacity (RBC) until reaching the Recommended Replacement Time (RRT) and $I_{IMD}$ is the average current projected to be consumed by the device (i.e., the IMD) during that timeframe, which can also be referred to as the device current. The $I_{IMD}$ can include, e.g., background operational current, pacing current, telemetry current, etc. However, this simple approach of Equation 1 cannot easily accommodate more realistic scenarios in which the magnitude of the actual device current changes during that timeframe, e.g., due to a transition to a different charge pump level as the battery voltage decreases. Nor does this simple approach accommodate the reality that the $RBC_{RRT}$ is not a constant, but is actually a function of $I_{IMD}$. These simplifications thus may introduce additional error into the projected longevity estimate. To the extent that these simplifications generally underestimate the magnitude of $I_{IMD}$ across at least a portion of the timeframe of interest, and to the extent that increased $I_{IMD}$ generally decreases RBC, these simplifications likely overestimate the projected longevity estimate that gets reported to a user.

Embodiments of the present technology that are described herein provide for more robust and accurate approaches to determining a longevity estimate of a battery powered IMD.

Embodiments of the present technology that are described herein can be used determine a device longevity estimate for an IMD without having to assume a static system (e.g., without assuming a constant time-averaged device current, etc.). While these embodiments are a bit more involved than a simple approach that uses Equation 1, they have the substantial advantage of being more accurate, especially when the demand on the battery changes during the time interval of interest.

Starting from first-principles, current from the battery is the rate of change of charge (Q; aka capacity) of the battery, which is specified below in Equation 2.

$$I_{batt} = dQ_{batt}/dt. \quad \text{(Eq. 2)}$$

In Equation 2, and other equations, $I_{batt}$ is the current from the battery, and $Q_{batt}$ is the remaining charge (i.e., capacity) of the battery. Rearranging Equation 2 results in Equation 3, shown below.

$$dt = dQ_{batt}/I_{batt}. \quad \text{(Eq. 3)}$$

Therefore, the total time (T) it is estimated to take to discharge the battery from some starting capacity level ($Q_i$) to a subsequent capacity level ($Q_f$), aka $T_{Qi \rightarrow Qf}$, can be computed as specified below in Equation 4a, which can alternatively be represented as shown below in Equation 4b.

$$\int_{Q_i}^{Q_f} dt = \int_{Q_i}^{Q_f} \frac{dQ_{batt}}{I_{batt}} \quad \text{(Eq. 4a)}$$

$$T_{Q_i \rightarrow Q_f} = \int_{Q_i}^{Q_f} \frac{dQ_{batt}}{I_{batt}}. \quad \text{(Eq. 4b)}$$

Note that while the endpoints for the above integrals are specified in terms of battery charge, one or both of these endpoints could instead be specified in terms of battery voltage ($V_{batt}$), since the relationship between $V_{batt}$ and $Q_{batt}$ is essentially a monotonic function, as can be appreciated from FIGS. 1A and 1B. Thus, for example, if endpoint $Q_f$ is associated with RRT and the RRT threshold is specified in terms of a battery voltage level $V_{RRT}$, then the inverse relationship described by FIGS. 1A and 1B could be used to establish $Q_f = Q_{batt}(V_{RRT})$.

Since a battery is used to power an IMD, the current supplied by the battery ($I_{batt}$) is equal to the current consumed by the IMD ($I_{IMD}$). In other words, $I_{batt}$ equals $I_{IMD}$. Thus, Equation 4b can be rewritten as shown below in Equation 5.

$$T_{Q_i \rightarrow Q_f} = \int_{Q_i}^{Q_f} \frac{dQ_{batt}}{I_{IMD}}. \quad \text{(Eq. 5)}$$

If $I_{IMD}$ is assumed to be a constant or otherwise independent of Q, then Equation 5 can be rewritten as Equation 6 shown below.

$$T_{Q_i \rightarrow Q_f} = \frac{Q_f - Q_i}{I_{IMD}}. \quad \text{(Eq. 6)}$$

However, the assumption that $I_{IMD}$ can be treated as a constant between $Q_i$ and $Q_f$ is not generally appropriate. In other words, this is an example of an oversimplification that can introduce errors into longevity predictions. While the device's programmed parameters might not change during an interval of interest (e.g., between $Q_i$ and $Q_f$), other factors do change that might impact the device's current requirements. Perhaps the most prominent factor that changes as a function of $Q_{batt}$ is $V_{batt}$, as can be appreciated from FIGS. 1A and 1B. It is also noted that it is often the case that certain functions performed by an IMD are modulated based on the most recent measurement of $V_{batt}$. For example, a charge pump level employed by a pacemaker to support a pace pulse amplitude of 2.5V will likely increase as $V_{batt}$ decreases from above 2.5V to below 2.5V (this is a simplified example; in reality, the transition of charge pump level changes when $V_{batt}$ decreases through a slightly higher threshold level, with that buffer added to accommodate non-ideal efficiencies, etc.). Additional device-based actions that are dependent on $V_{batt}$ will also likely exist.

To make the dependency of $I_{IMD}$ on $Q_{batt}$ through $V_{batt}$ more explicit, Equation 5, discussed above, can be rewritten as Equation 7 shown below.

$$T_{Q_i \rightarrow Q_f} = \int_{Q_i}^{Q_f} \frac{dQ_{batt}}{I_{IMD}(V_{batt}(Q_{batt}))}. \quad \text{(Eq. 7)}$$

It is noted that the value of $I_{IMD}$ may be dependent on more factors than just $V_{batt}$. However, for much of the discussion herein, the dependency on $V_{batt}$ is primarily focused on. Moreover, those other factors are generally not dependent on $Q_{batt}$, and thus are invariant with respect to the integration.

In accordance with certain embodiments of the present technology, a way to solve Equation 7 is by determining periods during which $I_{IMD}$ is (or can be treated as being) independent of $V_{batt}$ (and thus independent of $Q_{batt}$), and then performing piecewise integration of those separate pieces. Equation 8a, shown below, can be used to perform the piecewise integration of those separate pieces. Each integral in Equation 8a can be simplified similar to how Equation 6 was solved, resulting in Equation 8b shown below.

$$T_{Q_i \rightarrow Q_f} = \int_{Q_i}^{Q_A} \frac{dQ_{batt}}{I_{IMD\_1A}} + \int_{Q_A}^{Q_B} \frac{dQ_{batt}}{I_{IMD\_AB}} + \int_{Q_B}^{Q_C} \frac{dQ_{batt}}{I_{dev\_BC}} + \ldots + \int_{Q_Z}^{Q_f} \frac{dQ_{batt}}{I_{dev\_Z2}} \quad \text{(Eq. 8a)}$$

$$T_{Q_i \rightarrow Q_f} = \frac{\Delta Q_{int1}}{I_{IMD\_int1}} + \frac{\Delta Q_{int2}}{I_{IMD\_int2}} + \ldots + \frac{\Delta Q_{intN}}{I_{IMD\_intN}}, \quad \text{(Eq. 8B)}$$

where $I_{IMD\_intn}$ is a current consumed by the IMD during an $n^{th}$ one of the N intervals ($int_1$, $int_2$, ... $int_N$), and $\Delta Q_{intn}$, is a change in capacity (e.g., capacity consumed) during the $n^{th}$ one of the N intervals ($int_1$, $int_2$, ... $int_N$).

Thus, for example, if an IMD's charge pump level was the only factor that was dependent on $V_{batt}$, then these separate pieces could represent each of the possible discrete charge pump levels.

One way to implement Equation 8b is to tabulate (either ahead of time or on-demand) all of the voltages at which an IMD could transition to a different operating current, determine the value of $Q_{batt}$ associated with those voltages (e.g., using a battery performance profile relationship, an example of which is illustrated in FIGS. 1A and 1B), and then complete that table of operating currents based on the individual voltage levels, selected programmed parameters, and any other known factors that influence the magnitude of that current (e.g., relative pacing burden, etc.). With this information, a partial duration can be computed for each row of the table, and then a total duration can be computed by summing partial durations from all of the rows with $Q_{batt}$ values between $Q_i$ and $Q_f$. In accordance with certain embodiments, linear or higher-order interpolations can be utilized for the first and last partial durations if $Q_i$ and/or $Q_f$ do not land exactly on a table boundary.

In accordance with certain embodiments that are especially useful where it is not possible or easy to determine discrete periods used to employ the approach of Equation 8b, a generalized approach to solving Equation 7 is to use one of the many known techniques to numerically integrate Equation 7. For example, one approach is to discretize the integral into a summation shown below in Equation 9a:

$$T_{Q_i \to Q_f} = \int_{Q_i}^{Q_f} \frac{dQ_{batt}}{I_{IMD}(V_{batt}(Q_{batt}))} \approx \sum_{Q=Q_i}^{Q_f} \frac{\Delta Q}{I_{IMD}(V_{batt}(Q))}. \quad \text{(Eq. 9a)}$$

Performing the summation defined in Equation 9a for an appropriate value of $\Delta Q$ will result in a robust estimate of the total duration between $Q_i$ and $Q_f$ (that is, $T_{Q_i \to Q_f}$).

One of the advantages of the approaches described above is that they can easily provide a longevity estimate between any two battery capacity limits or battery voltage limits or combinations thereof (e.g., BOS to RRT, RRT to EOS, etc.).

Figure 3:
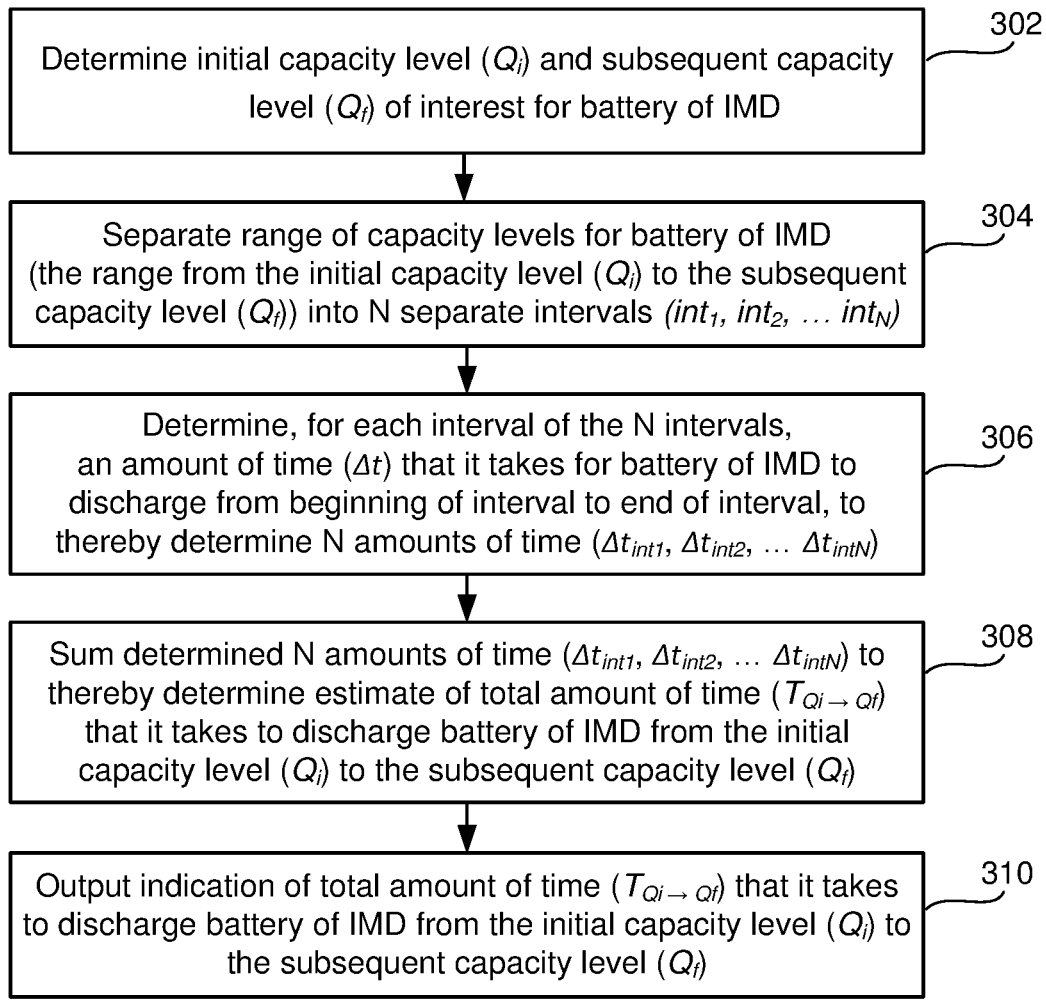
FIG. 3 is a high level flow diagram that is used to summarize methods for estimating the longevity of an IMD in accordance with certain embodiments of the present technology.

Certain embodiments of the present technology, which were introduced above in the discussion of Equations 1 through 9a, will now be summarized with reference to the high level flow diagram of FIG. 3. More specifically, FIG. 3 is used to summarize methods for estimating a longevity of an IMD that is powered by a battery. In accordance with certain embodiments, such a method can be performed by an external device (e.g., external programmer) that wirelessly communicates with an IMD that is powered by a battery. It would also be possible that such a method is performed by an IMD that is powered by a battery, or by a combination of an IMD powered by a battery and an external device that wirelessly communication with the IMD powered by the battery. Other variations are also possible and within the scope of the embodiments described herein. Regardless of what device(s) performs one of the methods summarized with reference to FIG. 3, such a method can be for use with an IMD that is powered by a battery.

Referring to FIG. 3, step 302 involves determining an initial capacity level ($Q_i$) and a subsequent capacity level ($Q_f$) of interest for a battery of an IMD whose longevity is being estimated. Step 302 can be performed, e.g., by accepting indications of the initial capacity level ($Q_i$) and the subsequent capacity level ($Q_f$) of interest from a user (e.g., a clinician) via an user interface of an external programmer (or other external device) that is configured to wirelessly communicate with the IMD for which longevity is being estimated. For an example, the initial capacity level ($Q_i$) for the battery of the IMD can correspond to a capacity level of the battery at a Beginning of Service (BOS), and the subsequent capacity level ($Q_f$) for the battery of the IMD can correspond to a capacity level of the battery at a Recommended Replacement Time (RRT). For another example, the initial capacity level ($Q_i$) for the battery of the IMD can correspond to a capacity level of the battery at a present time, and the subsequent capacity level ($Q_f$) for the battery of the IMD can correspond to a capacity level of the battery at an End of Service (EOS). More generally, the initial capacity level ($Q_i$) for the battery of the IMD can correspond to a capacity level of the battery at a BOS, a capacity level of the battery at a present time, or some other specified capacity level; and the subsequent capacity level ($Q_f$) for the battery of the IMD can correspond to a capacity level of the battery at a RRT, a capacity level at an EOS, or some other specified capacity level that differs from the initial capacity level ($Q_i$). As part of or prior to step 302, a user can be provided with a plurality of different selectable options for the initial capacity level ($Q_i$) and a plurality of different selectable options for the subsequent capacity level ($Q_f$). Alternatively, or additionally, a user can be provided with a plurality of different options for combinations of the initial capacity level ($Q_i$) and the subsequent capacity level ($Q_f$). Such options can be provided via a display or other user interface of an external programmer or some other external (i.e., non-implantable) device. Such options can be provided, e.g., via a pulldown menu, a scrolling menu, virtual buttons, and/or the like, but are not limited thereto. Another alternative is that one or more of these capacity levels ($Q_i$ and/or $Q_f$) is/are predefined for the IMD, and may or may not be modifiable by a user, depending upon the specific implementation.

Still referring to FIG. 3, step 304 involves separating a range of capacity levels for the battery of the IMD (which range extends from the initial capacity level ($Q_i$) for the battery to the subsequent capacity level ($Q_f$) for the battery) into a number (N) of separate intervals ($int_1$, $int_2$, ... $int_N$), wherein N is an integer that is equal to or greater than 3. For each interval of the N intervals, there is a respective beginning and end of the interval and a respective estimated current ($I_{IMD}$) consumed by the IMD during the interval that may differ from a current consumed by the IMD during other ones of the N intervals. In accordance with certain embodiments, the range of capacity levels for the battery is separated into the N separate intervals at step 304 such that for each interval, of the N intervals, the current ($I_{IMD}$) consumed by the IMD remains substantially constant during the interval. The term "remains substantially constant", as the term is used herein (e.g., in the phrase "the current ($I_{IMD}$) consumed by the IMD remains substantially constant during the interval"), means remains within a specified percent of a starting value. Depending on the specific implementation, the specified percent can be +/−3 percent, +/−5 percent, or +/−10 percent, or +/− some other specified percent that is no greater than 10 percent. Depending on the specific implementation, sizes of the N of separate intervals ($int_1$, $int_2$, ... $int_N$) can be the same as or different from one another. In certain embodiments, in order to separate the range of capacity levels into the N separate intervals, such that the current ($I_{IMD}$) consumed by the IMD remains substantially constant within each of intervals, small enough intervals of a same duration can be selected such that the $I_{IMD}$ does not have a chance to significantly change during the interval. Alternatively, this can be achieved more intelligently by taking into account a battery profile and/or other factors to identify intervals of likely different durations within which the $I_{IMD}$ remains substantially the same, likely resulting in fewer total number N of separate intervals. An example of such other factors relates to when it is likely that there will be a discontinuity in the $I_{IMD}$, e.g., because of a change in operation of the IMD and/or because of the battery voltage falling below a specified level, but is not limited thereto. The value of the $I_{IMD}$ that is consumed during one of the intervals can be, e.g., that value of the $I_{IMD}$ at the start of that interval, or some average (i.e., mean) or median of the $I_{IMD}$ over that interval, but is not limited thereto. Other variations are also possible and within the scope of the embodiments described herein.

Where it is desired that the initial capacity level ($Q_i$) for the battery of the IMD corresponds to a capacity level of the battery at a present time, there are various different ways to determine the capacity level of the battery at the present time. For example, an IMD can keep track of an estimate of the total cumulative charge consumed from the battery so far. Alternatively, or additionally, an IMD can keep track of a total number of pace events and/or a total number of sense events, and can provide such number(s) to an external programmer, and based on such number(s) the external programmer can estimate the total cumulative charge consumed from the battery so far, and can also estimate a background current drain so far, and such estimates can be used to estimate the capacity level of the battery at the present time. Other variations are also possible and are within the scope of the embodiments described herein.

Still referring to FIG. 3, step 306 involves determining, for each interval of the N intervals, an amount of time (Δt) that it is estimated to take for the battery to discharge from the beginning of the interval to the end of the interval, and thereby determining N amounts of time ($\Delta t_{int1}$, $\Delta t_{int2}$, ... $\Delta t_{intN}$). In accordance with certain embodiments, step 306 is accomplished by determining, for each interval of the N intervals, a quotient of a total capacity consumed during the interval divided by the respective estimated current ($I_{IMD}$) consumed by the IMD during the interval.

Step 308 involves summing the determined N amounts of time ($\Delta t_{int1}$, $\Delta t_{int2}$, ... $\Delta t_{intN}$) to thereby determine an estimate of a total amount of time ($T_{Qi \to Qf}$) that it takes to discharge the battery from the starting capacity level ($Q_i$) to the subsequent capacity level ($Q_f$), wherein the total amount of time ($T_{Qi \to Qf}$) is indicative of a longevity of the IMD that is powered by the battery. In other words, the total amount of time ($T_{Qi \to Qf}$) can be used as an estimate of a longevity of the IMD.

In accordance with certain embodiments, steps 306 and 308 are collectively performed using Equation 8c shown below (which is equivalent to Equation 8b discussed above, but with different nomenclatures being used):

$$T_{Q_i \to Q_f} = \frac{\Delta Q_{int1}}{I_{IMD\_int1}} + \frac{\Delta Q_{int2}}{I_{IMD\_int2}} + \ldots + \frac{\Delta Q_{intN}}{I_{IMD\_intN}}. \quad \text{(Eq. 8c)}$$

In Equation 8c, shown above, $I_{IMD\_int1}$ is the current consumed by the IMD during the internal $int_1$, $I_{IMD\_int2}$ is the current consumed by the IMD during the internal $int_2$, ... $I_{IMD\_intN}$ is the current consumed by the IMD during the internal $int_N$. More generally, $I_{MD\_int\_n}$ is the current consumed by the IMD during one of the N intervals ($int_1$, $int_2$, ... $int_N$).

Alternatively, in accordance with certain embodiments, steps 306 and 308 are collectively performed using Equation 9b shown below (which is equivalent to Equation 9a discussed above, but with different nomenclatures being used):

$$T_{Q_i \to Q_f} \approx \sum_{Q=Q_i}^{Q_f} \frac{\Delta Q}{I_{IMD}(V_{batt}(Q))}. \quad \text{(Eq. 9b)}$$

where,
$I_{IMD}(V_{batt}(Q))$ is a current consumed by the IMD at least in part as a function of voltage of the battery at the capacity level Q, and
ΔQ is a change in capacity.

In Equation 9b, shown above, $I_{IMD}(V_{batt}(Q))$ is the current consumed by the IMD as a function of the voltage of the battery at the capacity level Q.

Step 310 involves outputting, via a user interface of an external device (e.g., an external programmer), an indication of the total amount of time ($T_{Qi \to Qf}$) that it is estimated to take to discharge the battery of the IMD from the starting capacity level ($Q_i$) to the subsequent capacity level ($Q_f$). For example, this may involve displaying, on a display of an external programmer, an indication of a total amount of time it will take to discharge a battery of an IMD from a present time to an RRT, or from a present time to an EOS. Other examples of the starting capacity level ($Q_i$) and the subsequent capacity level ($Q_f$) were discussed above, and thus need not be repeated. Multiple instances of such a method can be performed so that more than one type of indication of a longevity of an IMD powered by a battery is determined and provided to a user via a user interface. For an example, a user can be provided with both an indication of a total amount of time it will take to discharge a battery of an IMD from a present time to an RRT, as well as from the present time to the EOS, both of which are indicative of a remaining longevity of the IMD. The longevity from a beginning of service (BOS) to the EOS is often referred to as the projected service life (PSL). The longevity from a present time to the RRT can be referred to as a remaining longevity until RRT. The longevity from the RRT to the EOS is often referred to as the prolonged service period (PSP). These are just a few examples of the types of longevity that can be estimated using embodiments of the present technology described herein.

Since the battery of an IMD is being used to power the IMD, at any point in time the current consumed by the IMD is substantially the same as the current drawn from the battery. As can be appreciated from FIGS. 2A and 2B and their above discussion, a performance profile for a battery is dependent on the current drawn from the battery. Accordingly, a performance profile for a battery is dependent on the current consumed by the IMD (since at any point in time current consumed by the IMD is substantially the same as current drawn from the battery). Accordingly, to increase the accuracy of longevity estimates, it would be beneficial to take into account variations or changes over time in the current being drawn from the battery of the IMD. In accordance with certain embodiments of the present technology, this is achieved by using appropriate portions of the battery's performance profile when estimating the total amount of time ($T_{Qi \to Qf}$) that it takes to discharge the battery of the IMD from the starting capacity level ($Q_i$) to the subsequent capacity level ($Q_f$). More specifically, in accordance with certain embodiments, for each interval of the N intervals ($int_1$, $int_2$, ... $int_N$), when determining the amount of time (Δt) that it is estimated to take for the battery to discharge from the beginning of the interval to the end of the interval, a respective portion of the performance profile for the battery that corresponds to the current being drawn from the battery during the interval is used to determine the amount of time (Δt) that it is estimated to take for the battery to discharge from the beginning to the end of the interval.

Explained another way, certain embodiments of the present technology also provide for further enhancements by taking into account that battery performance profiles (e.g., $V_{batt}$ VS $Q_{batt}$, an example of which is illustrated in FIGS. 1A and 1B) are themselves a function of the magnitude of the current being drawn from the battery, $I_{batt}$ (as can be appreciated from FIGS. 2A and 2B). Thus, one way to incorporate this profile dependency into the analyses above is to maintain a family of performance profile curves, each representing the performance profile of the battery at different values of $I_{batt}$, and then use the most-appropriate performance profile curve for each step of the analysis based the current magnitude of $I_{batt}$ (which, as noted above, is equivalent to limp). If the current magnitude of $I_{batt}$ is in-between those that have been used to develop the family of profile curves, then a linear or non-linear interpolation can be performing using one or two or more adjacent profile curves to estimate the desired value.

Another way to incorporate this profile dependency on $I_{batt}$ is to leverage the fact that some battery chemistries that are used in IMDs discharge at relatively low rates that are dominated by Tafel kinetics. Lithium carbon monofluoride (Li-CFx) is one such chemistry well modeled with Tafel kinetics, as described in an article by Davis S, Takeuchi E S, Tiedemann W, Newman J., titled "Simulation of the LiCFx System", Journal of the Electrochemical Society. 2007 May 1; 154(5):A477-80. Use of this knowledge provides a way to directly transform a single profile curve produced at one specific value of $I_{batt}$ to that for another specific value of $I_{batt}$. As noted above, it is assumed that $I_{batt}$ and $I_{IMD}$ are the same.

Another approach to determining an estimate of the total amount of time ($T_{Qi \to Qf}$) that it takes to discharge the battery of an IMD from an initial capacity level ($Q_i$) to a subsequent capacity level ($Q_f$), is to integrate a different variant of Equation 2. A different rearrangement of Equation 2 results in Equation 10, shown below.

$$dQ_{batt} = I_{IMD}(V_{batt}(Q_{batt})) \cdot dt \qquad (Eq. 10)$$

Equation 10 can be rewritten in a discrete form to generate the following iterative Equation 11a, shown below. Further, since $\Delta Q = I_{IMD}(V_{batt}(Q_n))*\Delta t$, Equation 11a can be rewritten as Equation 11b, shown below.

$$Q_{n+1} = Q_n + \Delta Q \qquad (Eq. 11a)$$

$$Q_{n+1} = Q_n + I_{IMD}(V_{batt}(Q_n)) \cdot \Delta t \qquad (Eq. 11b)$$

In accordance with certain embodiments of the present technology, $Q_n$ is initialized with $Q_i$, and Equation 11b is run iteratively using a selected value for $\Delta t$ until $Q_{n+1}$ reaches $Q_f$. At that point, the total duration between $Q_i$ and $Q_f$ (that is, $T_{Qi \to Qf}$) is equal to n·$\Delta t$. An example of a selected value for $\Delta t$ is one month (i.e., 0.0833 years), but larger or smaller values for $\Delta t$ can alternatively be used. In accordance with certain embodiments, interpolation can be used to determine an appropriate fractional value of $\Delta t$ that might be more appropriate for the last iteration step if $Q_{n+1}$ does not fall exactly on $Q_f$.

In Equation 11b, $Q_n$ is a specified capacity level for the battery that changes from one iteration of the iterative equation to a next iteration of the iterative equation, $\Delta t$ is a specified duration of time that remains the same from one iteration of the iterative equation to a next iteration of the iterative equation, $V_{batt}(Q_n)$ is a voltage of the battery at the capacity level $Q_n$, ($V_{batt}(Q_n)$ is a current consumed by the IMD as a function of the voltage of the battery at the capacity level $Q_n$, and N is how many iterations of the iterative equation are computed until $Q_{n+1}$ reaches the specified subsequent capacity level ($Q_f$) for the battery.

In accordance with certain embodiments of the present technology that utilize Equation 11b, the estimate of a total amount of time ($T_{Qi \to Qf}$) that it takes to discharge the battery from the initial capacity level ($Q_i$) to the subsequent capacity level ($Q_f$) (which is indicative of a longevity of the IMD that is powered by the battery), is determined by determining a product of N multiplied by the specified duration of time ($\Delta t$). In other words, the product of N multiplied by the specified duration of time ($\Delta t$) can be used as (or to determine) the estimate of the total amount of time ($T_{Qi \to Qf}$) that it takes to discharge the battery from the initial capacity level ($Q_i$) to the subsequent capacity level ($Q_f$), wherein the total amount of time ($T_{Qi \to Qf}$) is indicative of a longevity of the IMD that is powered by the battery. As noted above, interpolation can be used to determine an appropriate fractional value of $\Delta t$ that might be more appropriate for the last iteration step if $Q_{n+1}$ does not fall exactly on $Q_f$. Examples of the initial capacity level ($Q_i$) for the battery of the IMD and examples of the subsequent capacity level ($Q_f$) for the battery of the IMD were discussed above, and thus, need not be described again.

Figure 4:
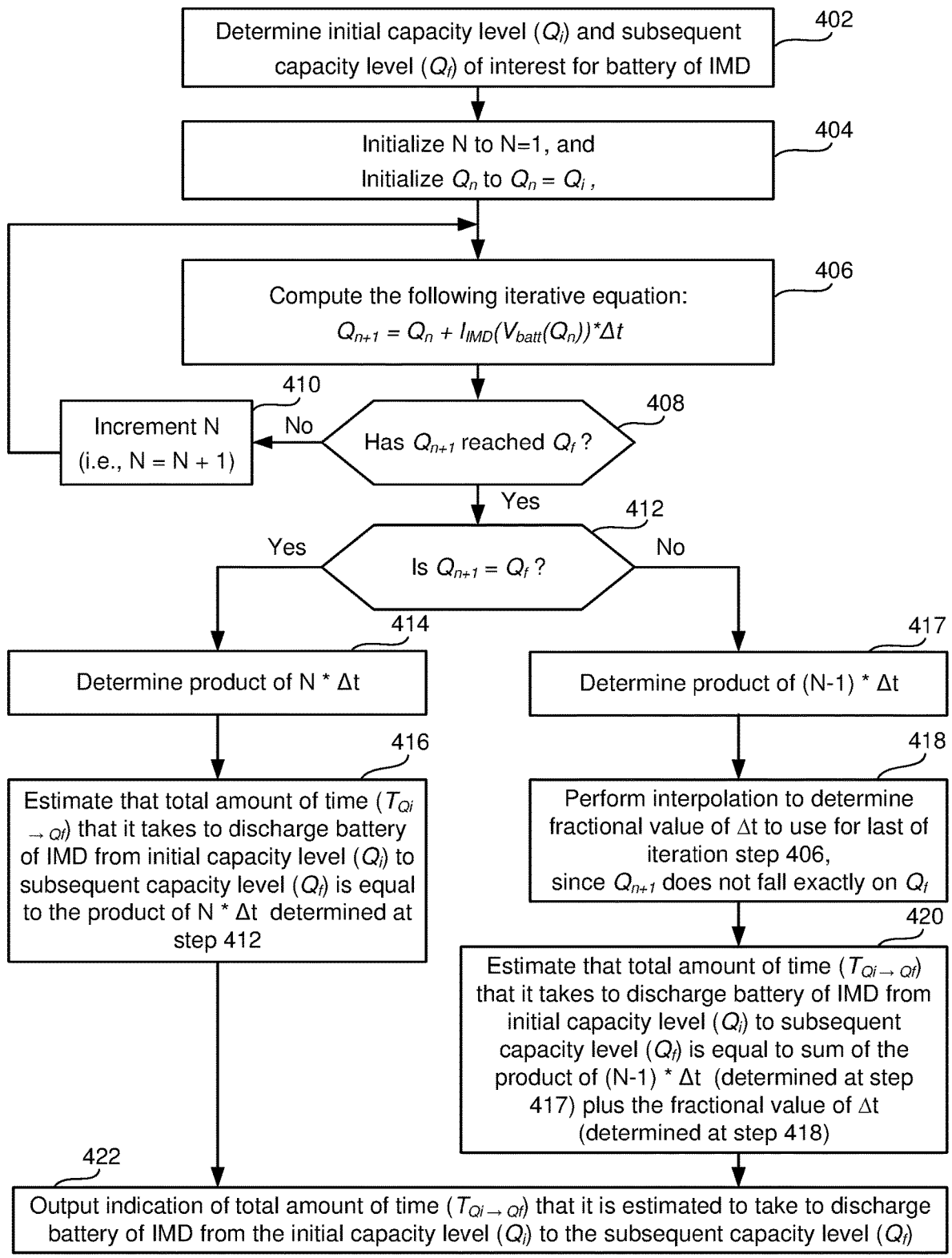
FIG. 4 is a high level flow diagram that is used to summarize methods for estimating the longevity of an IMD in accordance with certain alternative embodiments of the present technology.

Embodiments of the present technology that use Equation 11b are summarized with reference to FIG. 4. Referring to FIG. 4, step 402 involves determining an initial capacity level ($Q_i$) and a subsequent capacity level ($Q_f$) of interest for a battery of an IMD whose longevity is being estimated. Step 402 is the same as step 302 discussed above with reference to FIG. 3, and thus, additional details of step 402 can be appreciated from the above discussion of step 302, and need not be repeated.

Still referring to FIG. 4, step 404 involves initializing N to N=1, and initializing $Q_n$ to $Q_n = Q_i$. Step 406 involves computing the iterative Equation 11b (discussed above).

Step 408 involves determining whether $Q_{n+1}$ (calculated at step 406) has reached the subsequent capacity level ($Q_f$) of interest for the battery of the IMD whose longevity is being estimated. In certain embodiments, step 408 can be performed by determining whether $Q_{n+1}$ is equal to or has passed $Q_f$. If the answer to step 408 is No, then at step 410 the number N is incremented (i.e., N=N+1), and then step 406 is repeated. If the answer to step 408 is Yes, then flow goes to step 412.

Step 412 involves determining whether $Q_{n+1}$ (calculated at step 406) is equal to the subsequent capacity level ($Q_f$) of interest for the battery of the IMD whose longevity is being estimated. If the answer to step 412 is Yes, then at step 412 there is a determination of the product of N*$\Delta t$. As noted above, an example at is one month, but alternative durations of times (e.g., one week, two weeks, etc.) can be used for $\Delta t$. Then at step 416, it is estimated that the total amount of time ($T_{Qi \to Qf}$) that it takes to discharge the battery from the initial capacity level ($Q_i$) to the subsequent capacity level ($Q_f$) is equal to the product of N*$\Delta t$ that was determined at step 414. If the answer to step 412 is No, then at step 417 there is a determination of the product of (N−1)*$\Delta t$, and then at step 418 an interpolation is performed to determine a fractional value for $\Delta t$ to use for a last iteration of step 406, or more generally, to add to the product determined at step 417. Still referring to FIG. 4, step 420 involves estimated that the total amount of time ($T_{Qi \to Qf}$) that it takes to discharge the battery from the initial capacity level ($Q_i$) to the subsequent capacity level ($Q_f$) as being equal to the product of (N−1)*$\Delta t$ (that was determined at step 412) plus the fraction value for $\Delta t$ (determined at step 418). In other words, step 418 is used to achieve a last iteration of the iterative equation of step 406. In alternative embodiments, which are somewhat less accurate, steps 412, 417, 418 and 420 are eliminated and flow goes directly from step 408 to step 414 (or steps 414 and 416 are combined into a single step). Other variations are also possible and within the scope of the embodiments described herein.

Step 422 involves outputting, via a user interface of an external device (e.g., an external programmer), an indication of the total amount of time ($T_{Qi \to Qf}$) that it is estimated to take to discharge the battery of the IMD from the starting capacity level ($Q_i$) to the subsequent capacity level ($Q_f$).

Step 422 is the same as step 310 discussed above with reference to FIG. 3, and thus, additional details of step 422 can be appreciated from the above discussion of step 310, and need not be repeated.

Depending upon the specific implementation, the order of the various steps shown in FIGS. 3 and 4 can be rearranged, and thus, embodiments are not intended to be limited to the order shown in FIGS. 3 and 4. It would also be possible that just subsets of the steps shown in FIGS. 3 and 4 be performed. Other variations of the methods summarized with reference to FIGS. 3 and 4 could be appreciated from the above discussion. For example, certain steps can be separated into multiple steps. Further, logic associated with certain determination can be modified yet still provide the same or similar results. For example, the determination at step 408 could alternatively be whether the $Q_{n+1}$ is greater than $Q_\beta$, in which case the Yes and No branches can be reversed.

Figure 5:
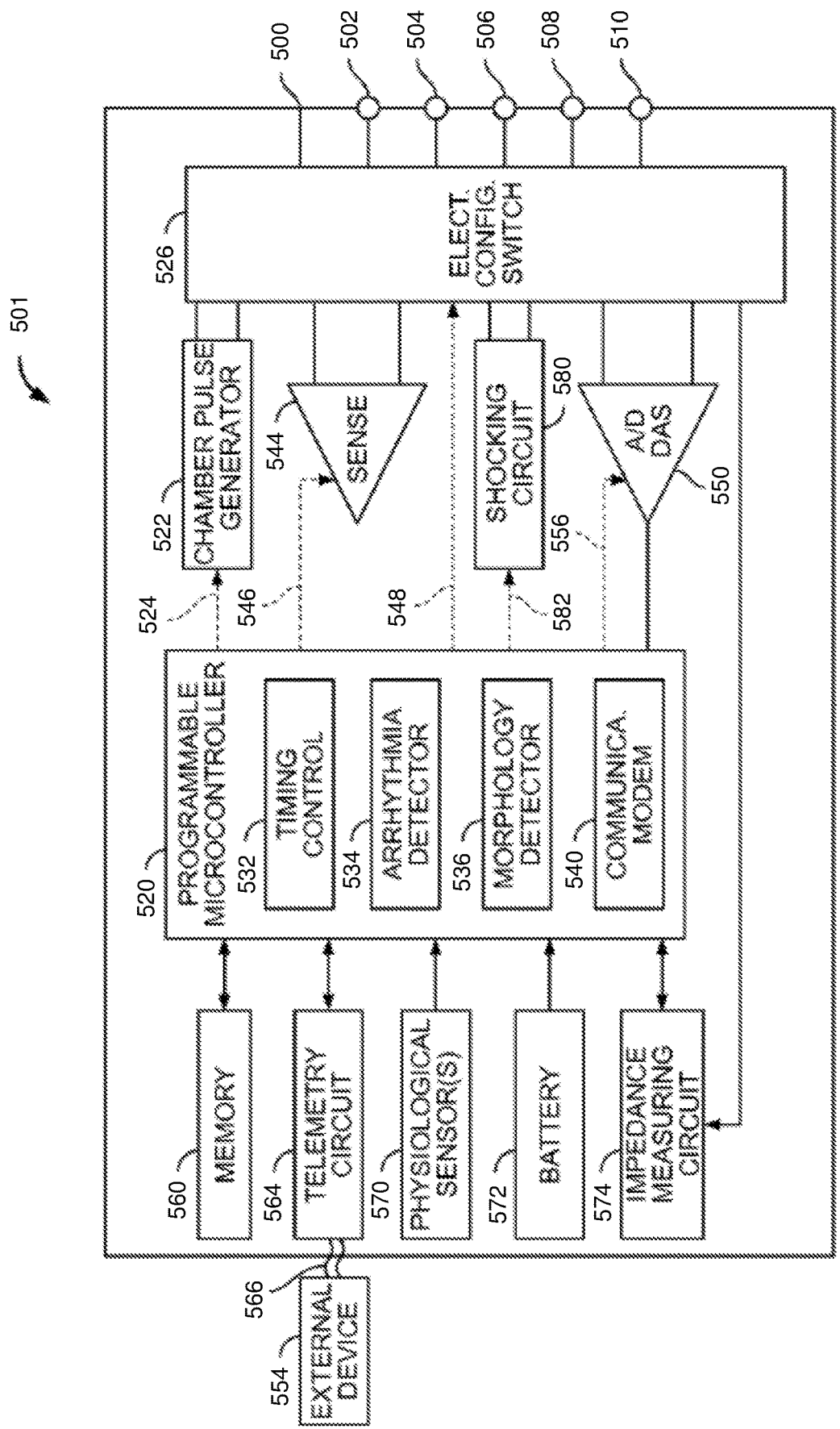
FIG. 5 shows a high level block diagram of one embodiment of an IMD for which longevity can be estimated using embodiments of the present technology.

FIG. 5 shows a block diagram of one embodiment of an IMD 501 that is implanted into the patient as part of the implantable system in accordance with certain embodiments herein. More specifically, the IMD 501 is an example of an IMD for which a longevity (e.g., remaining longevity) can be estimated using embodiments of the present technology described herein. The IMD 501 can be, for example, a pacemaker that is configured to be implanted in a pectoral region of a patient, a leadless pacemaker configured to be implanted within or attached to a cardiac chamber of a patient's heart, an ICD, or a patient monitoring device that does not provide therapy, but is not limited thereto. Certain components of the IMD 501 shown in FIG. 5 can be eliminated if the features performed by such components are not needed, as would be the case if the IMD was a patient monitoring device that does not provide therapy. It would also be possible for the IMD 501 to include additional components that are not shown in FIG. 5, as would be appreciated by one of ordinary skill in the art. It would also be possible for embodiments of the present technology to be used with IMDs that are not cardiac stimulation type devices, but rather, are neurostimulation devices, such as, but not limited to, spinal cord stimulation (SCS) devices, or deep brain stimulation (DBS) devices.

Referring to FIG. 5, the IMD 501 has a housing 500 to hold the electronic/computing components. Housing 500 (which is often referred to as the "can", "case", "encasing", or "case electrode") may be programmably selected to act as the return electrode for certain stimulus modes. Housing 500 may further include a connector (not shown) with a plurality of terminals 502, 504, 506, 508, and 510. The terminals may be connected to electrodes that are located in various locations on housing 500 or elsewhere within and about the heart. The IMD 501 includes a programmable microcontroller 520 that controls various operations of the IMD 501, including cardiac monitoring and stimulation therapy. Microcontroller 520 includes a microprocessor (or equivalent control circuitry), RAM and/or ROM memory, logic and timing circuitry, state machine circuitry, and I/O circuitry.

The IMD 501 further includes a first pulse generator 522 that generates stimulation pulses for delivery by one or more electrodes coupled thereto. Pulse generator 522 is controlled by microcontroller 520 via control signal 524. Pulse generator 522 may be coupled to the select electrode(s) via an electrode configuration switch 526, which includes multiple switches for connecting the desired electrodes to the appropriate I/O circuits, thereby facilitating electrode programmability. Switch 526 is controlled by a control signal 528 from microcontroller 520.

In the embodiment of FIG. 5, a single pulse generator 522 is illustrated. Optionally, the IMD may include multiple pulse generators, similar to pulse generator 522, where each pulse generator is coupled to one or more electrodes and controlled by microcontroller 520 to deliver select stimulus pulse(s) to the corresponding one or more electrodes.

Microcontroller 520 is illustrated as including timing control circuitry 532 to control the timing of the stimulation pulses (e.g., pacing rate, atrio-ventricular (AV) delay, atrial interconduction (A-A) delay, or ventricular interconduction (V-V) delay, etc.). Timing control circuitry 532 may also be used for the timing of refractory periods, blanking intervals, noise detection windows, evoked response windows, alert intervals, marker channel timing, and so on. Microcontroller 520 also has an arrhythmia detector 534 for detecting arrhythmia conditions and a morphology detector 536. Although not shown, the microcontroller 520 may further include other dedicated circuitry and/or firmware/software components that assist in monitoring various conditions of the patient's heart and managing pacing therapies. More generally, the microcontroller can include one or more processors configured to provide certain features described herein.

The IMD 501 is further equipped with a communication modem (modulator/demodulator) 540 to enable wireless communication with the remote slave pacing unit. Modem 540 may include one or more transmitters and two or more receivers. In one implementation, modem 540 may use low or high frequency modulation. As one example, modem 540 may transmit implant-to-implant (i2i) messages and other signals through conductive communication between a pair of electrodes. Modem 540 may be implemented in hardware as part of microcontroller 520, or as software/firmware instructions programmed into and executed by microcontroller 520. Alternatively, modem 540 may reside separately from the microcontroller as a standalone component.

The IMD 501 includes a sensing circuit 544 selectively coupled to one or more electrodes, that perform sensing operations, through switch 526 to detect the presence of cardiac activity in the one or more chambers of the heart. Sensing circuit 544 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 526 determines the sensing polarity of the cardiac signal by selectively closing the appropriate switches. In this way, the clinician may program the sensing polarity independent of the stimulation polarity.

The output of sensing circuit 544 is connected to microcontroller 520 which, in turn, triggers or inhibits the pulse generator 522 in response to the presence or absence of cardiac activity. Sensing circuit 544 receives a control signal 546 from microcontroller 520 for purposes of controlling the gain, threshold, polarization charge removal circuitry (not shown), and the timing of any blocking circuitry (not shown) coupled to the inputs of the sensing circuitry.

In the embodiment of FIG. 5, a single sensing circuit 544 is illustrated. Optionally, the IMD may include multiple sensing circuits, similar to sensing circuit 544, where each sensing circuit is coupled to one or more electrodes and controlled by microcontroller 520 to sense electrical activity detected at the corresponding one or more electrodes. Sensing circuit 544 may operate in a unipolar sensing configuration or in a bipolar sensing configuration.

The IMD 501 further includes an analog-to-digital (ND) data acquisition system (DAS) 550 coupled to one or more electrodes via switch 526 to sample cardiac signals across any pair of desired electrodes. Data acquisition system 550 is configured to acquire intracardiac electrogram signals, convert the raw analog data into digital data, and store the digital data for later processing and/or telemetric transmission to an external device 554 (e.g., a programmer, local transceiver, or a diagnostic system analyzer). Data acquisition system 550 is controlled by a control signal 556 from the microcontroller 520.

Microcontroller 520 is coupled to a memory 560 by a suitable data/address bus. The programmable operating parameters used by microcontroller 520 are stored in memory 560 and used to customize the operation of the IMD 501 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 501 may be non-invasively programmed into memory 560 through a telemetry circuit 564 in telemetric communication via communication link 566 with external device 554. Telemetry circuit 564 allows intracardiac electrograms and status information relating to the operation of IMD 501 (as contained in microcontroller 520 or memory 560) to be sent to external device 554 through communication link 566. The external device 554 can estimate a longevity of the IMD 501.

The IMD 501 can further include magnet detection circuitry (not shown), coupled to microcontroller 520, to detect when a magnet is placed over the unit. A magnet may be used by a clinician to perform various test functions of the IMD 501 and/or to signal microcontroller 520 that external device 554 is in place to receive or transmit data to microcontroller 520 through telemetry circuits 564.

The IMD 501 can further include one or more physiological sensors 570. Such sensors are commonly referred to as "rate-responsive" sensors because they are typically used to adjust pacing stimulation rates according to the exercise state of the patient. However, physiological sensor 570 may further be used to detect changes in cardiac output, changes in the physiological condition of the heart, or diurnal changes in activity (e.g., detecting sleep and wake states). Signals generated by physiological sensors 570 are passed to microcontroller 520 for analysis. Microcontroller 520 responds by adjusting the various pacing parameters (such as rate, AV Delay, V-V Delay, etc.) at which the atrial and ventricular pacing pulses are administered. While shown as being included within the IMD 501, physiological sensor(s) 570 may be external to the IMD 501, yet still be implanted within or carried by the patient. Examples of physiologic sensors might include sensors that, for example, sense respiration rate, pH of blood, ventricular gradient, activity, position/posture, minute ventilation (MV), and so forth.

A battery 572 provides operating power to all of the components in IMD 501. Battery 572 is preferably capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 572 also desirably has a predictable discharge characteristic so that elective replacement time can be detected. As one example, IMD 501 employs lithium/silver vanadium oxide batteries. Exemplary performance profile curves for various different types of batteries, which can be used as the battery 572, are shown in and were described above with reference to FIGS. 1A, 1B, 2A and 2B. At any given time, the battery 572 will have a battery voltage (BV) and a remaining battery capacity (RBC).

The IMD 501 further includes an impedance measuring circuit 574, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 574 is coupled to switch 526 so that any desired electrode may be used. In this embodiment the IMD 501 further includes a shocking circuit 580 coupled to microcontroller 520 by a data/address bus 582.

Figure 6:
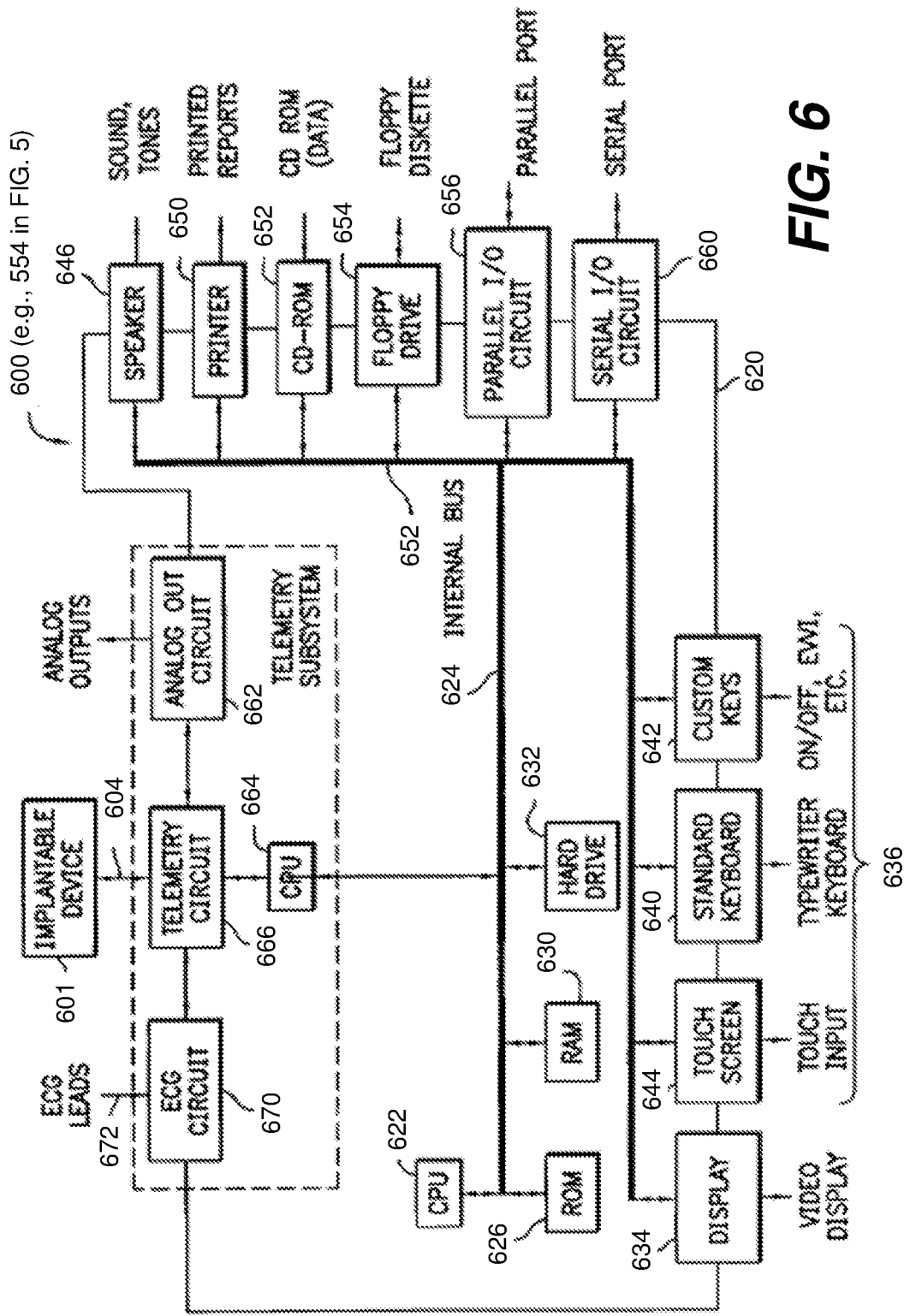
FIG. 6 shows a high level block diagram of one embodiment of an external device that can be used to determine and display estimates of longevity for IMDs in wireless communication with the external device, in accordance with certain embodiments of the present technology.

FIG. 6 is a functional block diagram of one embodiment of an external device 600 that can determine estimates of the longevity for one or more types of IMDs using embodiments of the present technology described herein. The external device 600 can be, e.g., a clinical programmer, a remote patient monitor, or a portable computing device, such as a smartphone, a tablet computer, or a laptop computer, but is not limited thereto. Embodiments of the present technology can also be used with other types of external devices that can wireless communication with IMDs in order to obtain measures of BV and stored historical data, and/or the like from IMDs.

Referring to FIG. 6, the external device 600 illustrating greater details thereof. A CPU 622 is in communication with an internal bus 624. The internal bus 624 provides a common communication link and power supply between the various electrical devices of the external device 600, including the CPU 622. The external device 600 also comprises memory and storage including ROM 626, RAM 630, and a hard drive 632 in communication with the internal bus 624. The ROM 626, RAM 630, and hard drive 632 provide temporary memory and non-volatile storage of data in a well-known manner. In particular, the ROM 626, RAM 630, and hard drive 632 can store programmed control programs and commands for upload to the IMD 501 as well as control programs for display of data received from the IMD 501 as is well understood in the art. It will be appreciated that, in certain embodiments, alternative data storage/memory devices, such as flash memory, can be included or replace at least one of the ROM 626, RAM 630, and hard drive 632 without detracting from the spirit of the invention. The CPU 622 can include one or more processors configured to provide certain features described herein.

The external device 600 also comprises a display 634. The display 634 is adapted to visually present graphical and alphanumeric data in a manner well understood in the art. For example, the display 634 can be used to display estimates of longevity for an IMD, but is not limited thereto.

In certain embodiments, the external device 600 also comprises input devices 136 comprising, in this embodiment, a keyboard 640, a plurality of custom keys 642, and a touchscreen 644 aspect of the display 634. The keyboard 640 facilitates entry of alphanumeric data into the programmer system 600. The custom keys 642 are programmable in order to provide one touch functionality of predefined functions and/or operations of the external device 600. The custom keys 642 may be embodied as dedicated touch keys and/or as predefined areas of the touchscreen 644.

In certain embodiments, the external device 600 also comprises a speaker 646 and a printer 650 in communication with the internal bus 624. The speaker 646 is adapted to provide audible alerts and signals to a user and the printer 650 is adapted to provide a printed read-out of information as generated or monitored by the external device 600.

The external device 600 can also comprise a CD drive 652 and a floppy drive 654 which together provide removable storage of data. The CD drive 652 and the floppy drive 654 provide removable data storage and read capability for the programmer system 600 in a well understood manner.

In this embodiment, the external device 600 also includes a parallel input-output (IO) circuit 656, a serial 10 circuit 660, and an analog output circuit 662. These circuits 656, 660, 662 provide a variety of communication capability with other devices in a manner well understood in the art.

In this embodiment, the external device 600 further includes a telemetry CPU 664 that is in communication with a telemetry circuit 666. The telemetry circuit 666 maintains the communication link 604 between the external device 600 and the IMD 501. This aspect of the invention enables the external device 600 and the IMD 501 to exchange information at an increased speed to enable real-time transmission of signals obtained from the at least physiological sensor 608.

In the example shown, the external device 600 also comprises an ECG circuit 670 in communication with a plurality of ECG leads 672. The ECG circuit 670 and the ECG leads 672 obtain electrical signals from the surface of a patient's body in a well understood manner and configure these signals for display as an ECG waveform 674 on the display 634 of the external device 600.

It is to be understood that the components of the external device 600 described above are exemplary and that additions or deletions of certain elements may be made without detracting from the spirit of the invention.

Another function that is provided, in certain embodiments, by the input devices 636 includes access to an automatic physician follow-up diagnostic to verify/monitor IMD operation, patient condition, records of past anomalous cardiac events, records of therapy provided, implantable device battery charge state, etc. The input devices 636 can also provide up-down scrolling through available functions or operations as well as selection of available functions.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means plus-function format and are not intended to be interpreted based on 35 U.S.C. § 112(f), unless and until such claim limitations expressly use the phrase "means for" followed by a statement of function void of further structure.

What is claimed is:

1. A method for use with an implantable medical device (IMD) that is powered by a battery, the method comprising:
   separating a range of capacity levels for the battery of the IMD, which said range extends from an initial capacity level ($Q_i$) for the battery to a subsequent capacity level ($Q_f$) for the battery, into a number (N) of separate intervals ($int_1$, $int_2$, ... $int_N$), such that for each interval, of the N intervals, a respective estimated current ($I_{IMD}$) consumed by the IMD remains substantially constant during the interval;
      wherein N is an integer that is equal to or greater than 3,
      wherein for each interval of the N intervals, there is a respective beginning and end of the interval, and
      wherein for one or more of the N intervals, the respective estimated current ($I_{IMD}$) consumed by the IMD during the interval differs from the estimated current consumed by the IMD during one or more other ones of the N intervals;
   determining, for each interval of the N intervals, an amount of time ($\Delta t$) that it is estimated to take for the battery to discharge from the beginning of the interval to the end of the interval, and thereby determining N amounts of time ($\Delta t_{int1}$, $\Delta t_{int2}$, ... $\Delta t_{intN}$); and
   summing the determined N amounts of time ($\Delta t_{int1}$, $\Delta t_{int2}$, ... $\Delta t_{intN}$) to thereby determine an estimate of a total amount of time ($T_{Qi \to Qf}$) that it takes to discharge the battery from the initial capacity level ($Q_i$) to the subsequent capacity level ($Q_f$), wherein the total amount of time ($T_{Qi \to Qf}$) is indicative of a longevity of the IMD that is powered by the battery.

2. The method of claim 1, wherein the determining, for each interval of the N intervals, the amount of time ($\Delta t$) that it is estimated to take for the battery to discharge from the beginning of the interval to the end of the interval, comprises determining a quotient of a total capacity consumed during the interval divided by the respective estimated current ($I_{IMD}$) consumed by the IMD during the interval.

3. The method of claim 1, wherein:
   the initial capacity level ($Q_i$) for the battery of the IMD corresponds to a capacity level of the battery at a Beginning of Service (BOS), a capacity level of the battery at a present time, or some other specified capacity level; and the subsequent capacity level ($Q_f$) for the battery of the IMD corresponds to a capacity level of the battery at a Recommended Replacement Time (RRT), a capacity level at an End of Service (EOS), or some other specified capacity level that differs from the initial capacity level ($Q_i$).

4. The method of claim 1, wherein:
sizes of the N of separate intervals ($int_1$, $int_2$, $int_N$) can be the same as or different from one another.

5. The method of claim 1, wherein
at any point in time current consumed by the IMD is substantially the same as current drawn from the battery;
a performance profile for the battery is dependent on the current drawn from the battery, and thus, is dependent on the current consumed by the IMD; and
for each interval of the N intervals, when determining the amount of time ($\Delta t$) that it is estimated to take for the battery to discharge from the beginning of the interval to the end of the interval, using a respective portion of the performance profile for the battery that corresponds to the current being drawn from the battery during the interval.

6. The method of claim 1, wherein the determining, for each interval of the N intervals, the amount of time ($\Delta t$) that it is estimated to take for the battery to discharge from the beginning of the interval to the end of the interval, and the summing the determined N amounts of time ($\Delta t_{int1}$, $\Delta t_{int2}$, ... $\Delta t_{intN}$) to thereby determine the estimate of the total amount of time ($T_{Qi \to Qf}$) that it takes to discharge the battery from the initial capacity level ($Q_i$) to the subsequent capacity level ($Q_f$), are collectively performed using the following equation:

$$T_{Qi \to Qf} = \frac{\Delta Q_{int1}}{I_{IMD\_int1}} + \frac{\Delta Q_{int2}}{I_{IMD\_int2}} + \ldots + \frac{\Delta Q_{intN}}{I_{IMD\_intN}},$$

where $I_{IMD\_intn}$ is an estimated current consumed by the IMD during an $n^{th}$ one of the N intervals ($int_1$, $int_2$, ... $int_N$), and $\Delta Q_{intn}$ is a change in capacity during the $n^{th}$ one of the N intervals ($int_1$, $int_2$, ... $int_N$).

7. The method of claim 1, wherein the determining, for each interval of the N intervals, the amount of time ($\Delta t$) that it is estimated to take for the battery to discharge from the beginning of the interval to the end of the interval, and the summing the determined N amounts of time ($\Delta t_{int1}$, $\Delta t_{int2}$, ... $\Delta t_{intN}$) to thereby determine the estimate of the total amount of time ($T_{Qi \to Qf}$) that it takes to discharge the battery from the initial capacity level ($Q_i$) to the subsequent capacity level ($Q_f$), are collectively performed using the following equation:

$$T_{Qi \to Qf} \approx \sum_{Q=Q_i}^{Q_f} \frac{\Delta Q}{I_{IMD}(V_{batt}(Q))},$$

where $I_{IMD}(V_{batt}(Q))$ is a current consumed by the IMD as a function at least in part of voltage of the battery at the capacity level Q, and $\Delta Q$ is a change in capacity.

8. The method of claim 1, wherein the method is performed by an external device configured to wireless communicate with the IMD that is powered by the battery, and further comprising outputting, via a user interface of the external device, an indication of the estimate of the total amount of time ($T_{Qi \to Qf}$) that it takes to discharge the battery from the initial capacity level ($Q_i$) to the subsequent capacity level ($Q_f$).

9. The method of claim 1, wherein sizes of at least some of the N of separate intervals ($int_1$, $int_2$, ... $int_N$) differ from one another.

10. An external device, comprising:
a telemetry subsystem configured to wirelessly communication with an implantable medical device (IMD) that is powered by a battery and implanted within a patient;
a display; and
at least one processor communicatively coupled to the telemetry subsystem and the display, the at least one processor configured to
separate a range of capacity levels for the battery of the IMD, which said range extends from an initial capacity level ($Q_i$) for the battery to a subsequent capacity level ($Q_f$) for the battery, into a number (N) of separate intervals ($int_1$, $int_2$, ... $int_N$), such that for each interval, of the N intervals, a respective estimated current ($I_{IMD}$) consumed by the IMD remains substantially constant during the interval
wherein N is an integer that is equal to or greater than 3, and
wherein for each interval of the N intervals, there is a respective beginning and end of the interval, and
wherein for one or more of the N intervals, the respective estimated current ($I_{IMD}$) consumed by the IMD during the interval differs from the estimated current consumed by the IMD during one or more other ones of the N intervals;
determine, for each interval of the N intervals, an amount of time ($\Delta t$) that it is estimated to take for the battery to discharge from the beginning of the interval to the end of the interval, and thereby determine N amounts of time ($\Delta t_{int1}$, $\Delta t_{int2}$, ... $\Delta t_{intN}$),
sum the determined N amounts of time ($\Delta t_{int1}$, $\Delta t_{int2}$, ... $\Delta t_{intN}$) to thereby determine an estimate of a total amount of time ($T_{Qi \to Qf}$) that it takes to discharge the battery from the initial capacity level ($Q_i$) to the subsequent capacity level ($Q_f$), wherein the total amount of time ($T_{Qi \to Qf}$) is indicative of a longevity of the IMD that is powered by the battery; and
cause to be displayed, on the display, an indication of the estimate of the total amount of time ($T_{Qi \to Qf}$) that it takes to discharge the battery from the initial capacity level ($Q_i$) to the subsequent capacity level ($Q_f$), which is indicative of the longevity of the IMD that is powered by the battery.

11. The external device of claim 10, wherein the at least one processor is configured to determine, for each interval of the N intervals, an estimate of the amount of time ($\Delta t$) that it takes for the battery to discharge from the beginning of the interval to the end of the interval, and is configured to sum the determined N amounts of time ($\Delta t_{int1}$, $\Delta t_{int2}$, ... $\Delta t_{intN}$) to thereby determine the estimate of the total amount of time ($T_{Qi \to Qf}$) that it takes to discharge the battery from the initial capacity level ($Q_i$) to the subsequent capacity level ($Q_f$), using the following equation:

$$T_{Qi \to Qf} = \frac{\Delta Q_{int1}}{I_{IMD\_int1}} + \frac{\Delta Q_{int2}}{I_{IMD\_int2}} + \ldots + \frac{\Delta Q_{intN}}{I_{IMD\_intN}},$$

where $I_{IMD\_int\_n}$ is an estimate of the current consumed by the IMD during an $n^{th}$ one of the N intervals ($int_1$, $int_2$, ... $int_N$), and $\Delta Q_{intn}$ is a change in capacity during the $n^{th}$ one of the N intervals ($int_1$, $int_2$, ... $int_N$).

12. The external device of claim 10, wherein the at least one processor is configured to determine, for each interval of the N intervals, an estimate of the amount of time ($\Delta t$) that it takes for the battery to discharge from the beginning of the interval to the end of the interval, and is configured to sum the determined N amounts of time ($\Delta t_{int1}$, $\Delta t_{int2}$, ... $\Delta t_{intN}$) to thereby determine the estimate of the total amount of time ($T_{Qi \to Qf}$) that it takes to discharge the battery from the initial capacity level ($Q_i$) to the subsequent capacity level ($Q_f$), using the following equation:

$$T_{Q_i \to Q_f} \approx \sum_{Q=Q_i}^{Q_f} \frac{\Delta Q}{I_{IMD}(V_{batt}(Q))},$$

where $I_{IMD}(V_{batt}(Q))$ is a current consumed by the IMD at least in part as a function of voltage of the battery at the capacity level Q, and $\Delta Q$ is a change in capacity.

13. The external device of claim 10, wherein the external device is selected from the group consisting of:
    an external clinical programmer;
    an in-home monitor; or
    a mobile computing device.

14. The external device of claim 10, wherein sizes of the N separate intervals ($int_1$, $int_2$, ... $int_N$) can be the same as or different from one another.

15. The external device of claim 10, wherein sizes of at least some of the N of separate intervals ($int_1$, $int_2$, ... $int_N$) differ from one another.

16. A method for use with an implantable medical device (IMD) that is powered by a battery, the method comprising:
    computing the following iterative equation $Q_{n+1} = Q_n + I_{IMD}(V_{batt}(Q_n)) \cdot \Delta t$ with $Q_n$ initialized with a specified initial capacity level ($Q_i$) for the battery,
    where
        $Q_n$ is a specified capacity level for the battery that changes from one iteration of the iterative equation to a next iteration of the iterative equation,
        $\Delta t$ is a specified duration of time that remains the same from one iteration of the iterative equation to a next iteration of the iterative equation,
        $V_{batt}(Q_n)$ is a voltage of the battery at the capacity level $Q_n$, and
        $I_{IMD}(V_{batt}(Q_n))$ is a current consumed by the IMD as a function of the voltage of the battery at the capacity level $Q_n$;
    repeating the iterative equation a plurality of times until $Q_{n+1}$ reaches a specified subsequent capacity level ($Q_f$) for the battery, to thereby determine a value for N, where N is how many iterations of the iterative equation are computed until $Q_{n+1}$ reaches the specified subsequent capacity level ($Q_f$) for the battery;
    wherein for one or more of the N iterations, the $I_{IMD}(V_{batt}(Q_n))$, which is the respective current consumed by the IMD as a function of the voltage of the battery at the capacity level $Q_n$, is different compared to the $I_{IMD}(V_{batt}(Q_n))$ for one or more other ones of the N iterations; and
    determining a product of N multiplied by the specified duration of time ($\Delta t$) to thereby determine an estimate of a total amount of time ($T_{Qi \to Qf}$) that it takes to discharge the battery from the initial capacity level ($Q_i$) to the subsequent capacity level ($Q_f$), wherein the total amount of time ($T_{Qi \to Qf}$) is indicative of a longevity of the IMD that is powered by the battery.

17. The method of claim 16, wherein:
    the initial capacity level ($Q_i$) for the battery of the IMD corresponds to a capacity level of the battery at a Beginning of Service (BOS), a capacity level of the battery at a present time, or some other specified capacity level; and
    the subsequent capacity level ($Q_f$) for the battery of the IMD corresponds to a capacity level of the battery at a Recommended Replacement Time (RRT), a capacity level at an End of Service (EOS), or some other specified capacity level that differs from the initial capacity level ($Q_i$).

18. The method of claim 16, further comprising:
    when $Q_{n+1}$ does not fall exactly on $Q_f$ during a last iteration of the iterative equation, using interpolation to determine a fractional value of $\Delta t$ corresponding to a last iteration of computing the iterative equation, and adding the fractional value of $\Delta t$ to the product of N−1 multiplied by the specified duration of time ($\Delta t$) to thereby determine the estimate of the total amount of time ($T_{Qi \to Qf}$) that it takes to discharge the battery from the initial capacity level ($Q_i$) to the subsequent capacity level ($Q_f$), wherein the total amount of time ($T_{Qi \to Qf}$) is indicative of the longevity of the IMD that is powered by the battery.

19. The method of claim 16, wherein the method is performed by an external device configured to wireless communicate with the IMD that is powered by the battery, and further comprising outputting, via a user interface of the external device, an indication of the total amount of time ($T_{Qi \to Qf}$) that it takes to discharge the battery from the initial capacity level ($Q_i$) to the subsequent capacity level ($Q_f$).

20. An external device, comprising:
    a telemetry subsystem configured to wirelessly communication with an implantable medical device (IMD) that is powered by a battery and implanted within a patient;
    a display; and
    at least one processor communicatively coupled to the telemetry subsystem and the display, the at least one processor configured to
    compute the following iterative equation $Q_{n+1} = Q_n + I_{IMD}(V_{batt}(Q_n)) \cdot \Delta t$ with $Q_n$ initialized with a specified initial capacity level ($Q_i$) for the battery,
    where
        $Q_n$ is a specified capacity level for the battery that changes from one iteration of the iterative equation to a next iteration of the iterative equation,
        $\Delta t$ is a specified duration of time that remains the same from one iteration of the iterative equation to a next iteration of the iterative equation,
        $V_{batt}(Q_n)$ is a voltage of the battery at the capacity level $Q_n$,
        $I_{IMD}(V_{batt}(Q_n))$ is a current consumed by the IMD as a function of the voltage of the battery at the capacity level $Q_n$, and
        N is how many iterations of the iterative equation are computed until $Q_{n+1}$ reaches the specified subsequent capacity level ($Q_f$) for the battery;
    repeat the iterative equation a plurality of times until $Q_{n+1}$ reaches a specified subsequent capacity level ($Q_f$) for the battery, to thereby determine a value for N, where N is how many iterations of the iterative equation are computed until $Q_{n+1}$ reaches the specified subsequent capacity level ($Q_f$) for the battery;

wherein for one or more of the N iterations, the $I_{IMD}(V_{batt}(Q_n))$, which is the respective current consumed by the IMD as a function of the voltage of the battery at the capacity level $Q_n$, is different compared to the $I_{IMD}(V_{batt}(Q_n))$ for one or more other ones of the N iterations;

determine a product of N multiplied by the specified duration of time ($\Delta t$) to thereby determine an estimate of a total amount of time ($T_{Qi \to Qf}$) that it takes to discharge the battery from the initial capacity level ($Q_i$) to the subsequent capacity level ($Q_f$), wherein the estimate of the total amount of time ($T_{Qi \to Qf}$) is indicative of a longevity of the IMD that is powered by the battery; and cause to be displayed, on the display, an indication of the estimate of the total amount of time ($T_{Qi \to Qf}$) that it takes to discharge the battery from the initial capacity level ($Q_i$) to the subsequent capacity level ($Q_f$), which is indicative of the longevity of the IMD that is powered by the battery.

21. The external device of claim 20, wherein:

the initial capacity level ($Q_i$) for the battery of the IMD corresponds to a capacity level of the battery at a Beginning of Service (BOS), a capacity level of the battery at a present time, or some other specified capacity level; and the subsequent capacity level ($Q_f$) for the battery of the IMD corresponds to a capacity level of the battery at a Recommended Replacement Time (RRT), a capacity level at an End of Service (EOS), or some other specified capacity level that differs from the initial capacity level ($Q_i$).

22. The external device of claim 20, wherein:

when $Q_{n+1}$ does not fall exactly on $Q_f$ during a last iteration of the iterative equation, the at least one processor is configured to use interpolation to determine a fractional value of $\Delta t$ corresponding to a last iteration of performing the iterative equation, and add the fractional value of $\Delta t$ to the product of N−1 multiplied by the specified duration of time ($\Delta t$) to thereby determine the estimate of the total amount of time ($T_{Qi \to Qf}$) that it takes to discharge the battery from the initial capacity level ($Q_i$) to the subsequent capacity level ($Q_f$), wherein the estimate of the total amount of time ($T_{Qi \to Qf}$) is indicative of the longevity of the IMD that is powered by the battery.

23. The external device of claim 20, wherein the external device is selected from the group consisting of:

an external clinical programmer;
an in-home monitor; or
a mobile computing device.

* * * * *